United States Patent [19]

Muchowski et al.

[11] Patent Number: 4,612,325

[45] Date of Patent: Sep. 16, 1986

[54] 5-AROYL-6-ALKYLTHIO-1,2-DIHYDRO-3H-PYRROLO(1,2-A)PYRROLE-1-CARBOXYLIC ACIDS AND USE THEREOF AS ANALGESICS AND ANTI-INFLAMMATORIES

[75] Inventors: Joseph M. Muchowski, Sunnyvale, Calif.; Robert Greenhouse, Coyoacan, Mexico

[73] Assignee: Syntex (U.S.A) Inc., Palo Alto, Calif.

[21] Appl. No.: 386,174

[22] Filed: Jun. 8, 1982

[51] Int. Cl.⁴ ................ C07D 403/04; A61K 31/395
[52] U.S. Cl. ..................................... 514/413; 548/453
[58] Field of Search ................ 548/468, 453; 514/413

[56] References Cited

U.S. PATENT DOCUMENTS 4,097,579  6/1978  Muchowski .......... 548/453
4,232,038  11/1980  Kluge et al. .......... 548/453
4,511,724  4/1985  Chang et al. .......... 548/452

OTHER PUBLICATIONS

Carmona et al. J. Org. Chem., 45, pp. 5336–5339 (1980).
Desales et al. J. Org. chem., 47, pp. 3668–3672 (1982).

Primary Examiner—Richard L. Raymond
Assistant Examiner—D. B. Springer
Attorney, Agent, or Firm—Tom M. Moran; Alan M. Krubiner

[57] ABSTRACT

Novel 5-aroyl-6-methylthio-, 6-methylsulfinyl-, or 6-methylsulfonyl-1,2-dihydro-3H-pyrrolo[1,2-a]pyrrole-1-carboxylic acids represented by the formulas

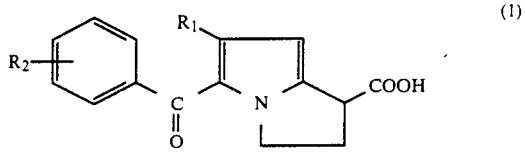

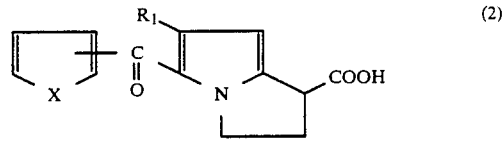

and the pharmaceutically acceptable, non-toxic esters and salts thereof, wherein $R_1$ is lower alkylthio, lower alkylsulfinyl, or lower alkylsulfonyl;

$R_2$ is hydrogen, hydroxy, lower alkyl, vinyl, cyclohexyl, cyclopropyl, lower alkoxy, fluoro, chloro, bromo, trifluoromethyl, trifluoromethoxy, nitro, amino, lower alkylcarbonylamino, lower alkylthio, lower alkylsulfonyl, or lower alkylsulfinyl;

X is oxygen, sulfur, N—$R_3$ where $R_3$ is hydrogen or lower alkyl.

This invention describes intermediates of the process and the process for the production of these compounds and their pharmaceutically acceptable non-toxic salts and pharmaceutical composition thereof. The claimed compounds are useful as anti-inflammatories and analgesics in mammals.

42 Claims, No Drawings

5-AROYL-6-ALKYLTHIO-1,2-DIHYDRO-3H-PYRROLO(1,2-A)PYRROLE-1-CARBOXYLIC ACIDS AND USE THEREOF AS ANALGESICS AND ANTI-INFLAMMATORIES

BACKGROUND OF THE INVENTION

1. Field of the Invention

This invention relates to novel 5-aroyl-6-alkylthio, 6-alkylsulfinyl and 6-alkylsulfonyl-1,2-dihydro-3H-pyrrolo[1,2-a]pyrrole-1-carboxylic acids and the pharmaceutically acceptable, non-toxic esters and salts thereof. The invention also relates to the intermediates necessary for the preparation of these compounds and to the processes for preparing the compounds of this invention. It further relates to the use of these compounds as anti-inflammatory agents, analgesic agents, antipyretic agents, platelet aggregation inhibitors, fibrinolytic agents and smooth muscle relaxants. The use of these compounds is both prophylactic and therapeutic. This invention still further relates to the pharmaceutical compositions comprising a compound of this invention and at least one pharmaceutical excipient.

2. Related Disclosures

Compounds which are structurally related to the instant invention are those which are represented by the formula

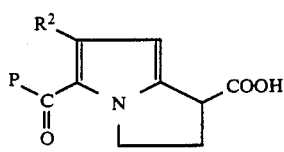

wherein P is a moiety selected from the group consisting of

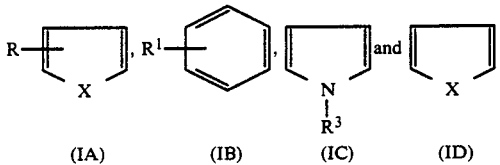

in which

X is oxygen or sulfur,

R is hydrogen, methyl, chloro or bromo, the R substitution being at the 3, 4 or 5 positions of the heterocyclic ring, $R^1$ is hydrogen, a lower alkyl group having 1 to 4 carbon atoms, a lower alkoxy group having from 1 to 4 carbon atoms, chloro, fluoro or bromo, the $R^1$ substitution being at the ortho, meta or para positions of the phenyl group, and $R^2$ and $R^3$ are each independently hydrogen or a lower alkyl group having from 1 to 4 carbon atoms.

The compounds represented by Formula (IA) and (ID) are disclosed in U.S. Pat. No. 4,087,539, issued May 2, 1978 to Muchowski et al, while compounds of Formulas (IB) and (IC) are disclosed in U.S. Pat. Nos. 4,089,969, issued May 16, 1978 to Muchowski et al and U.S. Pat. No. 4,097,579 issued June 27, 1978 to Muchowski et al, respectively.

Compounds of Formula (IB) wherein $R^1$ is methylthio are disclosed in co-pending U.S. application No. 71,444 filed Aug. 31, 1979, now abandoned, and compounds wherein $R^1$ is methylsulfinyl or methylsulfonyl are disclosed in U.S. Pat. No. 4,232,038, issued Nov. 4, 1980. All of these compounds are useful as anti-inflammatory agents, analgesic agents, platelet aggregation inhibitors, fibrinolytic agents and smooth muscle relaxants. They can be used both prophylactically and therapeutically.

SUMMARY

One aspect of this invention is a compound chosen from those represented by the formulas

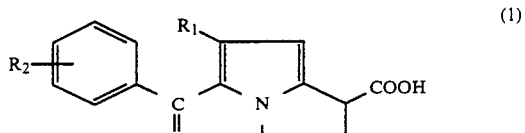

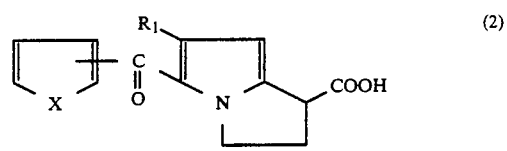

and the pharmaceutically acceptable non-toxic esters and salts thereof, wherein $R_1$ is lower alkylthio, lower alkylsulfinyl, or lower alkylsulfonyl;

$R_2$ is hydrogen, hydroxy, lower alkyl, vinyl, cyclohexyl, cyclopropyl, lower alkoxy, fluoro, chloro, bromo, trifluoromethyl, trifluoromethoxy, nitro, amino, lower alkylcarbonylamino, lower alkylthio, lower alkylsulfonyl or lower alkylsulfinyl;

X is oxygen, sulfur, N—$R_3$ where $R_3$ is hydrogen or lower alkyl.

Another aspect of this invention is a compound chosen from those represented by the formulas:

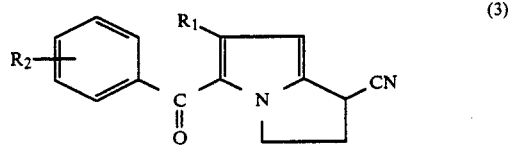

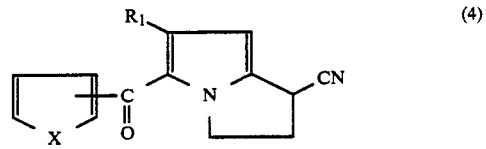

wherein $R_1$, $R_2$ and X are as defined above.

Yet another aspect of this invention is the process of making a compound of formula (1) or (2) or an acceptable non-toxic ester and salt thereof via synthetic pathways discussed hereafter.

A further aspect of the invention is the method of use of said compounds as anti-inflammatory agents, analgesic agents, antipyretic agents, vasospasm inhibitors, platelet aggregation inhibitors, fibrinolytic agents and as smooth muscle relaxants. The use is prophylactic and/or therapeutic.

The invention also relates to a preparation of pharmaceutical anti-inflammatory or analgesic compositions.

DETAILED DESCRIPTION OF THE INVENTION

Definitions

As used herein the pharmaceutically acceptable non-toxic salt derivatives of the compounds of formula (1) and formula (2) are those compounds wherein H of the COOH moiety in formula (1) or (2) is replaced by a positive ion such as sodium, for example, or is combined with a suitable amine. These are prepared as discussed hereafter in Examples 11 and 12 by reacting the acid of formula (1) or (2) with a suitable base.

The pharmaceutically acceptable non-toxic esters of formula (1) or (2) are those compounds wherein the OH of the COOH moiety in formula (1) or (2) is replaced by an alkoxy of 1 to 12 carbon atoms or an esterified glycerol. These are prepared as discussed hereinafter in Examples 9 and 10 by reacting an appropriate alcohol with the acid of formula (1) or (2).

The term "alkyl" refers to and includes branched and straight chain hydrocarbons containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

The term "lower alkyl" refers to a branched or unbranched saturated hydrocarbon chain of 1-6 carbon atoms such as, for example, methyl, ethyl, isopropyl, n-propyl, i-butyl, butyl, pentyl and the like.

"Vinyl" means monoethylenically unsaturated hydrocarbon of 2 carbons of formula —CH=CH$_2$.

"Cyclohexyl" means a saturated moncyclic hydrocarbon of 6 carbons without side chains.

"Cyclopropyl" means a saturated monocyclic hydrocarbon of 3 carbons without side chains.

The term "alkoxy" refers to a straight or branched chain alkyl ether groups wherein "alkyl" is as defined above. This includes radicals such as methoxy, ethoxy, 2-propoxy, butoxy, 3-pentoxy and the like.

"Lower alkoxy" means the group —OR wherein R is lower alkyl as herein defined.

"Aroyl" as used herein refers to the radical R—CO— wherein R is 5 or 6 carbon aromatic group. Exemplary compounds of aroyl are benzoyl, 2-furoyl, 2-thenoyl, 3-furoyl or 3-thenoyl and the like.

The term "alkylthio" as used hereinafter refers to straight or branched chain alkylthio ether group Z—S— wherein Z represents alkyl as defined above. Typical representatives are methylthio, ethylthio, propylthio, 2-propylthio, 2-butylthio, pentylthio, and the like.

The term "lower alkylthio" as used hereinafter refers to an alkylthio as defined hereinabove wherein an alkyl is alkyl having 1 to 5 carbon atoms such as methylthio, ethylthio, 2-propylthio, 2-butylthio or pentylthio.

The term "alkylsulfinyl" as used hereinafter refers to a straight or branched chain Z—S(O)— alkylsulfinyl group wherein Z represents alkyl as defined above.

The term "lower alkylsulfinyl" as used hereinafter refers to alkylsulfinyl having attached lower alkyl of 1 to 5 carbon atoms. Representative of alkylsulfinyls are, among others, methylsulfinyl, ethylsulfinyl, propylsulfinyl, and butylsulfinyl or pentylsulfinyl.

The term "alkylsulfonyl" as used hereinafter refers to compounds Z—S(O)$_2$— wherein Z represents alkyl as defined above.

The term "lower alkylsulfonyl" as used hereinafter refers to alkylsulfonyl as defined hereinbefore having attached lower alkyl of 1 to 5 carbon atoms. Typical representatives are methylsulfonyl, ethylsulfonyl, propylsulfonyl, butylsulfonyl and pentylsulfonyl.

"Trifluoromethyl" as used herein represents the substituent of formula F$_3$C—.

"Trifluoromethoxy" as used herein represents substituent of formula F$_3$CO—.

"Alkylcarbonylamino" as used hereinafter represents a substituent of formula Z—C(O)—NH— wherein Z represents alkyl as defined hereinbefore attached to the carbonyl group.

In naming the compounds of this invention IUPAC nomenclature is used. The substituent attached to the aromatic ring is identified by the number of the carbon atom on the aromatic ring to which the substituent is attached according to the following scheme illustrations:

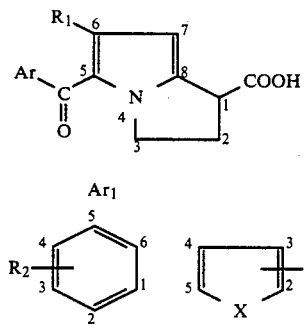

wherein R$_2$ and X are as defined in the Summary.

The R$_2$ substituent on the phenyl ring is at the ortho, meta or para positions.

The heterocyclic structures Ar$_2$ is attached to the 5-position of the pyrrolopyrrole structure either on the second or third carbon atom.

For example the compound is named 5-benzoyl-6-methylthio-1,2-dihydro-3H-pyrrolo[1,2-a]pyrrole-1-carboxylic acid when Ar is phenyl and R$_2$ is methylthio.

When Ar is 2-thenoyl and R$_2$ is methylthio the compound is named 5-(2-thenoyl)-6-methylthio-1,2-dihydro-3H-pyrrolo[1,2-a]pyrrole-1-carboxylic acid.

When Ar is 3-furoyl and R$_2$ is methylsulfonyl the compound is named 5-(3-furoyl)-6-methylsulfinyl-1,2-dihydro-3H-pyrrolo[1,2-a]pyrrole-1-carboxylic acid.

When Ar is N-methyl-2-pyrrolyl and R$_2$ is methylsulfonyl the compound is named 5-(N-methyl-2-pyrrolyl)-6-methylsulfonyl-1,2-dihydro-3H-pyrrolo[1,2-a]pyrrole-1-carboxylic acid.

Preferred Embodiments

The broadest aspect of this invention is given in the "Summary of the Invention" in this specification.

One preferred subclass of compounds of the invention is represented by nitriles of formula (3),

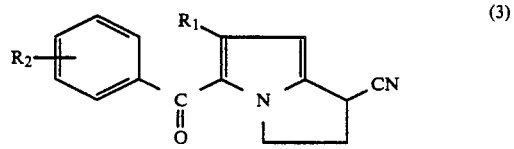

wherein R$_1$ and R$_2$ are as defined above in the Summary.

A preferred subgroup of this subclass includes nitriles of compounds of formula (1) wherein R₁ is methylthio, R₂ is hydrogen, fluoro, chloro or methoxy. This class encompasses but is not limited to the following compounds:
5-benzoyl-6-methylthio-1,2-dihydro-3H-pyrrolo[1,2-a]pyrrole-1-carbonitrile;
5-(4-fluorobenzoyl)-6-methylthio-1,2-dihydro-3H-pyrrolo[1,2-a]-pyrrole-1-carbonitrile;
5-(4-chlorobenzoyl)-6-methylthio-1,2-dihydro-3H-pyrrolo[1,2-a]-pyrrole-1-carbonitrile;
5-(4-methoxybenzoyl)-6-methylthio-1,2-dihydro-3H-pyrrolo[1,2-a]-pyrrole-1-carbonitrile;

Another preferred subclass of compounds of this invention is represented by alkylesters of compounds of formula (1)

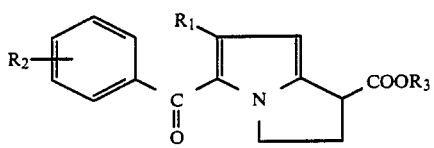

wherein R₁ and R₂ are as defined in the Summary and R₃ is lower alkyl.

One preferred subgroup of this subclass includes methylesters of compounds of formula (1) wherein R₁ is methylsulfinyl and R₃ is methyl. This subgroup encompasses compounds represented by
methyl 5-(4-bromobenzoyl)-6-methylsulfinyl-1,2-dihydro-3H-pyrrolo[1,2-a]pyrrole-1-carboxylate.

Another subgroup of this subclass includes methylesters of compounds of formula (1) wherein R₁ is methylsulfonyl and R₃ is methyl. This subgroup encompasses compounds represented by
methyl 5-(4-bromobenzoyl)-6-methylsulfonyl-1,2-dihydro-3H-pyrrolo[1,2-a]pyrrole-1-carboxylate.

The most preferred subgroup of this subclass includes methylesters of compounds of formula (1) wherein R₁ is methylthio, R₂ is methyl, bromo, vinyl, ethyl, ethoxy, i-propoxy, methylthio, trifluoromethyl, cyclohexyl, n-propyl, or cyclopropyl; and R₃ is methyl. This class encompasses but is not limited to the following compounds:
methyl 5-(4-methylthiobenzoyl)-6-methylthio-1,2-dihydro-3H-pyrrolo[1,2-a]pyrrole-1-carboxylate;
methyl 5-(4-trifluoromethylbenzoyl)-6-methylthio-1,2-dihydro-3H-pyrrolo[1,2-a]pyrrole-1-carboxylate;
methyl 5-(4-cyclohexylbenzoyl)-6-methylthio-1,2-dihydro-3H-pyrrolo[1,2-a]pyrrole-1-carboxylate;
methyl 5-(4-propylbenzoyl)-6-methylthio-1,2-dihydro-3H-pyrrolo[1,2-a]pyrrole-1-carboxylate;
methyl 5-(4-cyclopropylbenzoyl)-6-methylthio-1,2-dihydro-3H-pyrrolo[1,2-a]pyrrole-1-carboxylate;
methyl 5-(4-bromobenzoyl)-6-methylthio-1,2-dihydro-3H-pyrrolo[1,2-a]pyrrole-1-carboxylate;
methyl 5-(4-methylbenzoyl)-6-methylthio-1,2-dihydro-3H-pyrrolo[1,2-a]pyrrole-1-carboxylate;
methyl 5-(4-vinylbenzoyl)-6-methylthio-1,2-dihydro-3H-pyrrolo[1,2-a]pyrrole-1-carboxylate;
methyl 5-(4-ethylbenzoyl)-6-methylthio-1,2-dihydro-3H-pyrrolo[1,2-a]pyrrole-1-carboxylate;
methyl 5-(4-ethoxybenzoyl)-6-methylthio-1,2-dihydro-3H-pyrrolo[1,2-a]pyrrole-1-carboxylate;
methyl 5-(4-i-propoxybenzoyl)-6-methylthio-1,2-dihydro-3H-pyrrolo[1,2-a]pyrrole-1-carboxylate.

The most preferred subclass of compounds of this invention is represented by carboxylic acids of compounds of formula (1)

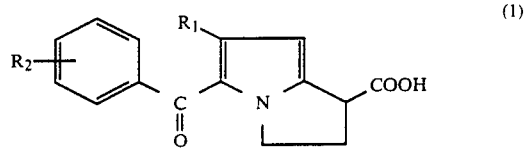

wherein R₁ and R₂ are as defined in the Summary.

One preferred subgroup of this subclass includes carboxylic acids of formula (1) wherein R₁ is methylsulfinyl and R₂ is bromo. This subgroup encompasses compounds represented by 5-(4-bromobenzoyl)-6-methylsulfinyl-6-methylthio-1,2-dihydro-3H-pyrrolo[1,2-a]pyrrole-1-carboxylic acid.

Another preferred subgroup of this subclass includes carboxylic acids of formula (1) wherein R₁ is methylsulfonyl and R₂ is bromo. This subgroup encompasses compounds represented by 5-(4-bromobenzoyl)-6-methylsulfonyl-6-methylthio-1,2-dihydro-3H-pyrrolo[1,2-a]pyrrole-1-carboxylic acid.

Most preferred compounds of this invention are those represented by compounds of formula (1) wherein R₁ is methylthio, R₂ is hydroxy, fluoro, chloro, methoxy, bromo, methyl, vinyl, ethyl, ethoxy, i-propoxy, methylthio, trifluoromethyl, cyclohexyl, n-propyl, or cyclopropyl. This subclass encompasses, but is not limited to, the following compounds:
5-benzoyl-6-methylthio-1,2-dihydro-3H-pyrrolo[1,2-a]pyrrole-1-carboxylic acid;
5-(4-fluorobenzoyl)-6-methylthio-1,2-dihydro-3H-pyrrolo[1,2-a]pyrrole-1-carboxylic acid;
5-(4-chlorobenzoyl)-6-methylthio-1,2-dihydro-3H-pyrrolo[1,2-a]pyrrole-1-carboxylic acid;
5-(4-methoxybenzoyl)-6-methylthio-1,2-dihydro-3H-pyrrolo[1,2-a]pyrrole-1-carboxylic acid;
5-(4-bromobenzoyl)-6-methylthio-1,2-dihydro-3H-pyrrolo[1,2-a]pyrrole-1-carboxylic acid;
5-(4-methylbenzoyl)-6-methylthio-1,2-dihydro-3H-pyrrolo[1,2-a]pyrrole-1-carboxylic acid;
5-(4-vinylbenzoyl)-6-methylthio-1,2-dihydro-3H-pyrrolo[1,2-a]pyrrole-1-carboxylic acid;
5-(4-ethylbenzoyl)-6-methylthio-1,2-dihydro-3H-pyrrolo[1,2-a]pyrrole-1-carboxylic acid;
5-(4-ethoxybenzoyl)-6-methylthio-1,2-dihydro-3H-pyrrolo[1,2-a]pyrrole-1-carboxylic acid;
5-(4-i-propoxybenzoyl)-6-methylthio-1,2-dihydro-3H-pyrrolo[1,2-a]pyrrole-1-carboxylic acid;
5-(4-methylthiobenzoyl)-6-methylthio-1,2-dihydro-3H-pyrrolo[1,2-a]pyrrole-1-carboxylic acid;
5-(4-trifluoromethylbenzoyl)-6-methylthio-1,2-dihydro-3H-pyrrolo[1,2-a]pyrrole-1-carboxylic acid;
5-(4-cyclohexylbenzoyl)-6-methylthio-1,2-dihydro-3H-pyrrolo[1,2-a]pyrrole-1-carboxylic acid;
5-(4-n-propylbenzoyl)-6-methylthio-1,2-dihydro-3H-pyrrolo[1,2-a]pyrrole-1-carboxylic acid; and
5-(4-cyclopropylbenzoyl)-6-methylthio-1,2-dihydro-3H-pyrrolo[1,2-a]pyrrole-1-carboxylic acid.

PREPARATION PROCEDURES

Preparation of alkylthio compounds

Compounds of formulas (1) and (2) where R₁ is alkylthio, R₂ is as defined in Summary, R₃ is lower alkyl and Ar is benzoyl, thenoyl, furoyl, pyrrolyl or N-alkylpyrrolyl are prepared by a process illustrated by Reaction Scheme I, Pathway 1 and Pathway 2.

Reaction Scheme I

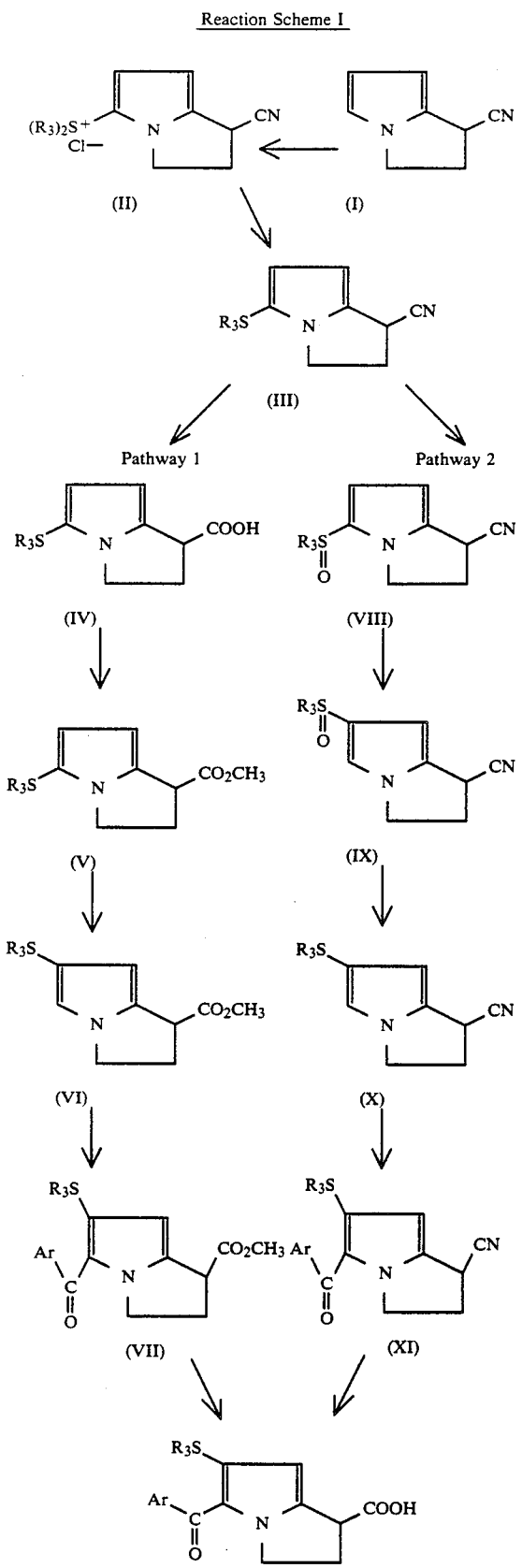

-continued
Reaction Scheme I formula (1) (2)

Initial steps leading to a compound of formula (III), are identical for both pathways.

Compound of formula (III) is prepared by condensation of compound of formula (I) with a dialkylsulfide to obtain compound of formula (II) which is thermally converted to compound of formula (III).

Compounds of formula (I) is reacted with the N-chlorosuccinimide dimethylsulfide adduct. This is accomplished by mixing previously precooled (in nitrogen atmosphere to −5° C. to −15° C., preferably −10° C.) N-chlorosuccinimide in dichloromethane with a solution of dialkylsulfide in anhydrous dichloromethane for about 5–30 minutes, preferably for 10 minutes. After further stirring for 5–30 minutes, preferably 10 minutes, at this temperature, the temperature is lowered to −35° C. to −65° C., preferably to −55° C., and a solution of 1,2-dihydro-3H-pyrrolo-[1,2-a]pyrrole-1-carbonitrile (I) in dry dichloromethane is added under constant stirring over a period of 5–20 minutes, preferably 10 minutes. Cooling is ceased and when the mixture reaches ambient temperature the solvent is removed in vacuo. Preparation of compound of formula (I) has been disclosed in U.S. Pat. No. 4,140,698 and is hereby incorporated by reference.

Obtained residual solid sulfonium salt (II) is suspended in an organic solvent, preferably toluene, and heated at reflux temperature in a nitrogen atmosphere for 2–10 minutes, preferably 5 minutes. The solvent is decanted, toluene is added and the mixture is heated at reflux temperature for 10–30 minutes, preferably 20 minutes. The toluene solutions are combined and evaporated. The residue is extracted into ether, preferably ethylether, and the ether solution is washed with water, dried and evaporated. This procedure yields an oil which is passed through a short column of silica gel with dichloromethane. The oil obtained in evaporation is sufficiently pure for use in the next reaction, but if necessary it may be purified by high pressure liquid chromatography (HPLC) using hexane ethyl acetate as a solvent. After HPLC on evaporation of the solvent a compound (III) is crystallized from the mixture of ether and organic solvent preferably ether-hexane.

Pathway 1

Through the Pathway 1 a compounds of formula (1) or (2) are prepared by hydrolysis of compound of formula (III), esterification of formula (IV), acid promoted rearrangement of formula (V) and subsequent reaction of compound of formula (VI) with an aryl carboxylic acid chloride.

The solution of carbonitrile (III) is reacted with a strong aqueous base such as 85% potassium hydroxide in water. The resulting solution is heated at reflux temperature for 6 to 10 hours, preferably for 8 hours. Alcohol is removed and the aqueous residue is extracted with ether. The aqueous phase is acidified to approximately pH 3 with strong acid such as 10% hydrochloric acid and the product is extracted into ethyl acetate. The extract is washed with water, dried, and evaporated in vacuo. The residual carboxylic acid (IV) is dissolved in ether and a molar excess of diazomethane in ether is added. When the reaction is completed, the solvent is removed yielding compound of formula (V) as an oily ester.

Methyl 6-alkylthio-1,2-dihydro-3H-pyrrolo[1,2-a]pyrrole-1-carboxylate (VI) is prepared by reacting a solution of the alkyl ester (V) in dichloromethane with acid, preferably trifluoroacetic acid. The mixture is stirred at room temperature for 0.25-2 hours, preferably 0.5 hour. A saturated solution of sodium bicarbonate in water is added, the organic phase is separated, dried, and evaporated. The residue is dissolved in dichloromethane and passed over a short column of neutral alumina to give a compound of formula (VI) as an oil.

Methyl 5-aroyl-6-methythio-1,2-dihydro-3H-pyrrolo(1,2-a)-pyrrole-1-carboxylate (VII) is prepared by acylation of compound (VI).

A reactive derivative of an appropriate aryl carboxylic acid, e.g. an aryl carboxylic acid chloride as specified in the Preparations, is added to a solution of the methyl ester (VI) in an anhydrous, organic hydrocarbon solvent such as toluene. The solution is heated in an inert atmosphere (e.g. nitrogen or argon) at a temperature and for a time sufficient to complete the reaction. Generally this will be about reflux temperature for 3 to 8 hours, depending on the compound. The solvent is removed and the residue is purified by methods known in the art, e.g., column chromatography on neutral alumina. The esters are eluted with an organic solvent, preferably with hexane-ethyl acetate.

The resulting esters (VII) are hydrolyzed to form carboxylic acid compound of formula (1) or (2).

To a solution of a methyl ester (VII) in an alcohol such as methanol, an aqueous base such as sodium hydroxide is added, and the resulting solution is stirred at a temperature of about 10°-30° C., preferably room temperature, for ½ to 18 hours. The alcohol is removed and the aqueous residue is extracted with an organic solvent such as ether. The aqueous alkaline phase is made acidic, e.g., with 10% hydrochloric acid, and the product is extracted into an organic solvent such as ethyl acetate. The final compounds of formula (1) or (2) are crystallized by procedures well documented in the art. Specific examples of this procedure are set forth hereafter in Examples 1-8.

Procedure for preparation of 5-substituted-1,2-dihydro-3H-pyrrolo-[1,2-a]pyrrole-1-carboxylic acid is described in U.S. patent application Ser. No. 06/198,552 (allowed April 1, 1982) which is hereby incorporated by reference.

Pathway 2

The Pathway 2 is an alternate pathway for the synthesis of alkylthio carboxylic acid compound of formula (1) and formula (2) via carbonitriles.

Through Pathway 2, the compounds of formula (1) or (2) are prepared by oxidation of compound of formula (III) to obtain compound of formula (VIII), acid promoted rearrangement of compound of formula (VIII), reduction of compound of formula (IX) and reaction of compound of formula (X) with an aryl carboxylic acid chloride and subsequent hydrolysis of compound of formula (XI).

To a solution of the compound of formula (III) in an alcohol such as methanol, cooled to 0° C., oxidizing agent such as sodium periodate dissolved in water is added over the period of 10 to 40 minutes, preferably 20 minutes under constant stirring. The cooling is removed and the mixture is stirred at room temperature for 2 to 5 hours, preferably 3 hours and the compound of formula (VIII) is recovered by means known in the art.

The conversion of the 5-alkylsulfinyl 1,2-dihydro-3H-pyrrolo[1,2-a]pyrrole-1-carbonitrile of formula (VIII) to the corresponding 6-alkylsulfinyl compound of formula (IX) is effected by reacting the compound of formula (VIII) with acid such as trifluoroacetic acid in an appropriate halogenated hydrocarbon solvent such as dichloromethane for about 0.5 to 3 hours at about 10°-50° C., preferably about 2 hours at ambient temperature. The solution is diluted with 200-300 ml of organic solvent preferably 250 ml of benzene, and evaporated. Obtained product is applied to a short column of silica gel, and the sulfoxide of formula (IX) is eluted with ethyl acetate-triethylamine.

The preparation of 6-alkylthio-carbonitrile compound (X) is effected using the reduction method of Olah et al, *Synthesis*, 137 (1978).

Powdered iodine, (0.5-3 eq., preferably 1 eq.), is added to a stirred solution of triphenylphosphine, (0.5-3 eq., preferably 1.15 eq.), in dry acetonitrile in an inert atmosphere, i.e., nitrogen. The sulfoxide (IX) (1 eq.) in dry acetonitrile (1-5 mmol/mmol sulfoxide, preferably 2.5 ml/mmol) and solid powdered sodium iodide (1-3 eq., preferably 2 eq.) are added. The reaction is completed in about 0.5 to 5 minutes, usually in 1 minute. After stirring for no more than 3 to 8 minutes, preferably for no more than 5 minutes, the solution is poured into a solution mixture of ether and 2% to 10% of aqueous sodium thiosulfate, preferably 5%. The ether phase is separated and washed with a 5% sodium bicarbonate solution, dried, and evaporated. The crude material is passed through a short column of silica gel, the product (X) is eluted with dichloromethane.

5-Aroyl-6-alkylthio-pyrrole-1-carbonitriles (XI) are prepared from compound (X) as follows. A solution of the crude sulfide (X) in xylene containing the appropriate acid chloride is heated at reflux temperature for 5 to 35 hours depending on compound. When the reaction is completed, an alcohol such as methanol is added to esterify the excess acid chloride and the mixture is evaporated. The residue is slurried with alumina and placed on top of a short column of alumina and the products are eluted with a suitable organic solvent system.

The 5-aroyl 6-alkylthio carboxylic acid of formula (1) or (2) is prepared by hydrolysis of the carbonitrile compounds (XI).

A solution of the nitrile (XI) (0.5- to 2 eq., preferably 1 eq.), in an alcohol such as ethanol containing a base such as sodium hydroxide and water, is heated at reflux temperature for 3 to 15 hours, depending on the compound. The alcohol is removed and the residual aqueous phase is diluted with water and extracted with ether. The aqueous alkaline phase is acidified with acid, preferably with 1N hydrochloric acid and the product is extracted into an organic solvent, preferably ethyl acetate, dried, and evaporated. The residual solid compound is crystallized from an organic solvent, preferably ethyl acetate.

Preparation of alkylsulfinyl compounds

5-Aroyl-6-alkylsulfinyl-1,2-dihydro-3H-pyrrolo[1,2-a]pyrrole-1-carboxylic acids are prepared in accordance with Pathway 1 of the Reaction Scheme I, to obtain compound of formula (VII). Thereafter, compound (VII) is converted into the sulfinyl compound according to the following reaction sequence.

Reaction Scheme II

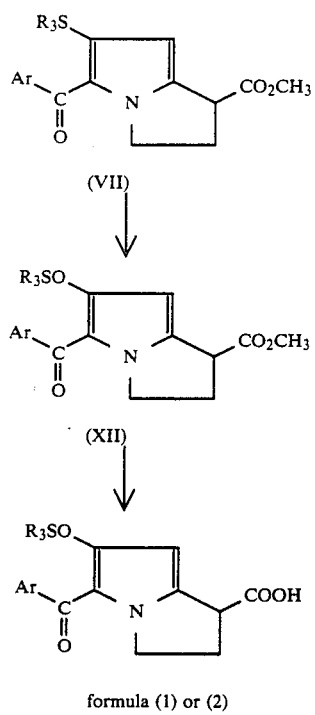

formula (1) or (2)

Reaction Scheme III

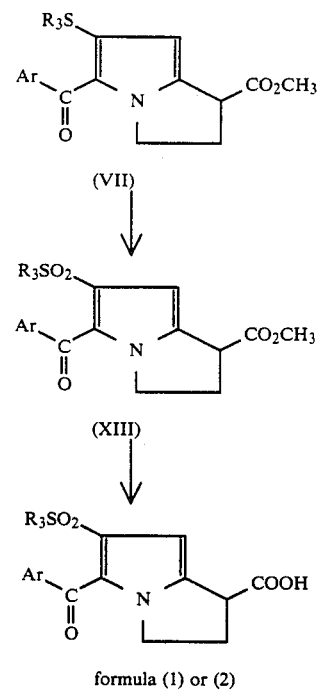

formula (1) or (2)

To a stirred suspension of methyl 5-aroyl-6-alkylthio-1,2-dihydro-3H-pyrrolo[1,2-a]pyrrole-1-carboxylate (VII) in alcohol, preferably methanol, is added an appropriate oxidizing agent, preferably sodium periodate in water at −5° C. to 5° C., preferably at 0° C. The mixture is left to come to a room temperature and the progress of the reaction is followed by thin-layer chromatography (TLC). Generally, the reaction is completed in 1 to 2 hours. Thereafter, the alcohol is removed under reduced pressure, the aqueous residue is saturated with sodium chloride and the product is extracted into an organic solvent, preferably ethyl acetate. The extract is washed with dilute sodium bicarbonate solution, with water, and dried.

Methyl 5-aroyl-6-alkylsulfinyl-1,2-dihydro-3H-pyrrolo-[1,2-a]pyrrole-1-carboxylate (XII) is yielded quantitatively. Compounds are crystallized from an alcohol such as methanol. The ester is converted to 5-aroyl-6-alkylsulfinyl-1,2-dihydro-3H-pyrrolo[1,2-a]pyrrole-1-carboxylic acid following the same procedure as outlined above in Reaction Scheme I for conversion of compound (VII) to compound of formula (1).

Preparation of alkylsulfonyl compounds

The 5-aroyl-6-alkylsulfonyl-1,2-dihydro-3H-pyrrolo[1,2-a]pyrrole-1-carboxylic acids are prepared in accordance with Pathway 1 of the Reaction Scheme I, steps (I) through step (VII). Thereafter, the compound (VII) is oxidized to the sulfonyl compound (XIII), which in turn is hydrolyzed to compound of formula (1) or (2) according to the following reaction steps.

To a stirred suspension of methyl 5-aroyl-6-alkythio-1,2-dihydro-3H-pyrrolo [1,2-a]pyrrole-1-carboxylate (VII) in anhydrous dichloromethane is added a solid oxidizing agent, preferably m-chloroperbenzoic acid at −5° C.-+5° C., preferably at 0° C. After 0.5 to 2 hours at 0° C., preferably after one hour, the solution is washed with diluted sodium bicarbonate solution and evaporated. The resulting compound methyl 5-aroyl-6-alkylsulfonyl-1,2-dihydro-3H-pyrrolo [1,2-a]pyrrole-1-carboxylate (XIII) is extracted from dichloromethanemethanol and the ester is converted to a carboxylic acid (1) or (2) following the same procedure as outline supra in Reaction Scheme I for conversion of compound (VII) to compound of formula (1) or (2). In this case a 5-aroyl-6-alkylsulfonyl- 1,2-dihydro-3H-pyrrolo[1,2-a]pyrrole-1-carboxylic acid is obtained.

It is to be understood that isolation of the compounds described herein, whether in the body of the specification or Examples, can be effected, if desired, by any suitable separation or purification procedure, such as, for example, filtration, extraction, crystallization, column chromatography, thin-layer chromatography or thick-layer chromatography, or a combination of these procedures. Specific illustrations of suitable separation and isolation procedures can be had by reference to the Procedures and Examples hereinbelow. However, other equivalent separation or isolation procedures could, of course, also be used.

The salts of said compounds are also isolated by conventional means. For example, the reaction mixtures are evaporated to dryness, and the salts can be further purified by conventional methods.

The pharmaceutically acceptable non-toxic salt derivatives of the compounds of formula (1) and (2) are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscilbe organic solvent, at a temperature of from about 0° C. to about 100° C., preferably at a room temperature. Typical inert, water-miscible organic solvents include methanol, ethanol, isopropanol, butanol, acetone, dioxane or tetrahydrofuran. The molar ratio of compounds of formula (1) or (2) to base used are chosen to provide the ratio desired for any particular salt. For preparing, for example, the calcium salts or magnesium salts the free acid starting material of formula (1) or (2) can be treated with at least one-half molar equivalent of pharmaceutically acceptable base to yield a neutral salt. When the aluminum salts of the compounds of formula (1) or (2) are prepared, at least one-third molar equivalent of the pharmaceutically acceptable base are employed if a neutral salt product is desired.

The salt derivatives of the compounds of formula (1) or (2) can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

The pharmaceutically acceptable non-toxic esters of formula (1) and (2) are prepared by esterifying the corresponding free acids with an alcohol reagent corresponding to the desired ester, e.g., an alkanol having up to 12 carbon atoms or with glycerol which is already esterified at two hydroxyls to other suitable acids. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichloroethane; or an ether solvent, e.g., diethyl ether, dibutyl ether dioxane, tetrahydrofuran, and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

The preferred acid esters are those ester derivatives prepared from methyl alcohol, ethyl alcohol, propyl alcohol, isopropyl alcohol, butyl alcohol, 2-butyl alcohol, isoamyl alcohol, pentyl alcohol, 2-pentyl alcohol, isopentyl alcohol, hexyl alcohol, 2-hexyl alcohol, isohexyl alcohol, heptyl alcohol, 2-heptyl alcohol, isoheptyl alcohol, octyl alcohol, 2-octyl alcohol, isooctyl alcohol, nonyl alcohol, 2-nonyl alcohol, isononyl alcohol, decyl alcohol, 2-decyl alcohol, isodecyl alcohol, undecyl alcohol, dodecyl alcohol, and the like.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

In summary, compounds of formula (1) or (2) or their pharmaceutically acceptable, non-toxic esters and salts are prepared by hydrolyzing the compound of formula (1) or (2), thereby yielding the corresponding free acid of formula (1) or (2); by esterifying an acid of formula (1) or (2) to yield the corresponding ester of formula (1) or (2); by converting an acid of formula (1) or (2) to the corresponding salt of formula (1) or (2); by hydrolyzing an ester or salt of formula (1) or (2) to yield the corresponding free acid of formula (1) or (2); by transesterifying an ester of formula (1) or (2) to yield a different ester; by converting an ester of formula (1) or (2) to the corresponding salt of formula (1) or (2); by converting a salt of formula (1) or (2) to the corresponding ester of formula (1) or (2); by converting a salt of formula (1) or (2) to a different salt; or by oxidizing a compound of formula (1) or (2) where $R_1$ is alkylthio to form a compound of formula (1) or (2) where $R_1$ is alkylsulfinyl or alkylsulfonyl.

Utility and Administration

The novel compounds of this invention, as defined hereinbefore, and their pharmaceutically acceptable non-toxic esters and salts are useful as analgesic agents, anti-inflammatory agents, antipyretic agents, vasospasm inhibitors, platelet aggregation inhibitors, fibrinolytic agents and as smooth muscle relaxants. Because of their potent anti-inflammatory and analgesic activities, they are preferably used as analgesic and/or anti-inflammatory agents. These compounds can be used both prophylactically and therapeutically.

The compositions containing these compounds are useful in the treatment and elimination of inflammation and/or pain. Thus, inflammatory conditions of the musculo-skeletal system, skeletal joints and other tissues such as inflammatory conditions including but not limited to rheumatism, contusion, laceration, arthritis, bone fractures, post-traumatic conditions, inflammation associated with bacterial infections, and gout are treated. Certain preferred compounds show analgesic and anti-inflammatory activity which is superior to certain related oompounds known in the art. Further, those particularly preferred compounds show even greater analgesic and anti-inflammatory activity as compared with related compounds known in the art as, for example, aspirin. In those cases in which the inflammatory conditions include pain and pyrexia coupled with the inflammation, the instant compounds are useful for the relief of these conditions as well as the inflammation. The compounds are also useful for treating pain which is not necessarily associated with inflammation, e.g., migraine, post-surgical pain, etc.

Small animal screening tests to determine anti-inflammatory activity potential include the carrageenin induced paw inflammation in the rat according to the method of Winter et al, [*Proc. Soc. Exp. Biol. Med.,* 111:544, (1962)]; the cotton pellet granuloma test in the rat according to the method of Meier et al, (*Experientia,* 6:469, (1950)) and modifications thereof; the adjuvant arthritis assay according to the method of Pearson [*Proc. Soc. Exp. Biol. Med.,* 91:95, (1956)]; and in vitro tests, for example, those using synovial explants from patients with rheumatoid arthritis, Dayer et al, [*J. Exp. Med.,* 145:1399, (1977)]. Small animal screening tests to determine analgesic activity potential include the mouse analgesic (anti-writing) assay according to the method of Hendershot and Forsaith [*J. Pharmacol. Exp. Ther.,* 125:237, (1959)].

Generally, the antipyretic activity potential is indicated by the anti-inflammatory potential as measured by the previously mentioned assays.

Platelet aggregation inhibition potential is determined by using turbidimetric method of Born (*J. Physiol. (London)*, 162:67p, (1962).

Potential activity as a smooth muscle relaxant is determined in vitro using the method of Vickery (*Prostaglandins Med.,* 2:299, (1979) or Vickery (*Prostaglandins Med.,* 2:225, (1979).

Administration of the active compounds of formula (1) or (2) and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof. Thus, for example, the composition can be administered orally, parenterally or topically, in the form of solid, semi-solid or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active ccmpound of formula (1) or (2) and the pharmaceutically acceptable non-toxic esters and salts thereof, and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administerable compositions can, for example, be prepared by dissolving, dispersing, etc. an active compound as defined above and optional pharmaceutical adjuvants in a carrier, such as. for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, (1975). The composition or formulation to be administered will, in any event, contain a quantity of the active compound(s) in an amount effective to alleviate the symptoms of the subject being treated.

The preferred manner of administration, for the conditions detailed above, is oral using a convenient daily dosage regimen which can be adjusted according to the degree of affliction. Generally, a daily dose of from 0.02 to 20 mg/kg of body weight per day of the active ccmpound of formula (1) or (2) and the pharmaceutically acceptable, non-toxic esters and salts thereof is used. Most conditions respond to treatment comprising a dosage level of the order of 0.02 to 2 mg per kilogram of body weight per day. Thus, for administration to a 70 kg person, the dosage range per day would be about 1.4 to 1400 mg per day, preferably about 3.5 to 140 mg per day.

For such oral administration, a pharmaceutically acceptable, non-toxic composition is formed by the incorporation of any of the normally employed excipients, such as, for example, pharmaceutical grades of mannitol, lactose, starch, magnesium stearate, sodium saccarine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

Generally, the pharmaceutically acceptable compositions will contain about 1% to about 90% by weight of the pharmaceutically active compound of this invention and 99% to 10% by weight of suitable pharmaceutical excipients. Preferably, the composition will be about 3.5 to 60% by weight of a pharmaceutically active compound, with the rest being suitable pharmaceutical excipients.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The active compounds of formula (1) or (2) and the pharmaceutically acceptable, non-toxic esters and salts thereof, may be formulated into a suppository using, for example, polyethylene glycols (PEG), for example, PEG 1000 (96%) and PEG 4000 (4%), as the carrier.

For systemic administration via suppository, traditional binders and carriers include, e.g. polyalkalene glycols or triglycerides. Such suppositories may be formed from mixtures containing active ingredient in the range of 0.5%–10%; preferably 1–2%.

Topical administration of the compounds of the instant invention include creams, ointments, lotions, emulsions, solutions, and the like in admixture with suitable pharmaceutically acceptable, non-toxic carrier or medicament vehicles. For example, a suitable ointment for topical application of compounds of the instant invention contains 15 to 45 percent of a saturated fatty alcohol having 16 to 24 carbon atoms such as cetyl alcohol stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behemic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding mono-ester of other fatty acids such as oleic acid and palmitic acid; and 0 to 20 wt. percent of a penetrant such as dimethyl sulfoxide, dimethylacetamide, dimethylformamide, and the like.

The concentration of compounds of formulas (1) or (2) or their pharmaceutically acceptable non-toxic salts in pharmaceutical compositions suitable for topical application will vary depending upon the particular activity of the steroid used in conjunction with the condition and subject to be treated. In general, topical preparations containing 0.005 to 5 mg of active compound preferably 0.1 to 1 mg active steroid are advantageously employed.

The following Preparations and Examples serve to illustrate the invention and make the invention enabling. They should not be construed as narrowing it or limiting its scope in any way.

In the Preparations and Examples, the use of Roman numerals refers to the reaction steps in Reaction Schemes.

PREPARATIONS

Preparations 1-3 describe the preparation of compounds which are intermediates in the synthesis of 5-aroyl-6-alkylthio-1,2-dihydro-3H-pyrrolo[1,2-a]pyrrole-1-carboxylic acid through Pathway 1. Preparations 4-6 describe the preparation of compounds which are intermediates in the synthesis of 5-aroyl-6-alkylthio-1,2-dihydro-3H-pyrrolo[1,2-a]pyrrole-1-carboxylic acid through Pathway 2.

PREPARATION 1

5-Alkylthio-1,2-dihydro-3H-pyrrolo[1,2-a]pyrrole-1-carbonitriles a.

5-Methylthio-1,2-dihydro-3H-pyrrolo[1,2-a]pyrrole-1-carbonitrile (III)

A solution of 1.15 g N-chlorosuccinimide in 40 ml of dry dichloromethane was cooled, in an atmosphere of nitrogen, to −10° C. (bath temp.) and a solution of 1 ml dimethylsulfide in 10 ml of anhydrous dichloromethane was added dropwise with stirring over a 10 min. period. After a further 10 min. at this temperature, the bath temperature was lowered to −55° C. and a solution of 1.08 g of 1,2-dihydro-3H-pyrrolo[1,2-a]pyrrole-1-carbonitrile (I) in 10 ml of dry dichloromethane was added with stirring over a 10 min. period. The cooling bath was then removed and when the internal temperature had reached ambient the solvent was removed in vacuo. The residual solid sulfonium salt (II) was suspended in toluene (100 ml) and heated at reflux temperature in a nitrogen atmosphere for 5 min. The solvent was decanted from an insoluble tar, 100 ml of toluene was added to the tar and the mixture was heated at reflux temperature for 20 min. The toluene solutions were combined and evaporated. The residue was taken up in ether, the ether solution was washed with water, dried over sodium sulfate and evaporated in vacuo to give an oil which was passed through a short column of silica gel with dichloromethane. The nearly colorless oil obtained on evaporation of the solvent (1.20 g) was sufficiently pure for use in the next reaction. For analysis a sample was purified by HPLC (lichrosorb column, 50 cm×⅜ in.) using hexane-ethyl acetate (85:15) as the eluting solvent at 1100 p.s.i.g. and a flow rate of 9.7 ml/min. The sulfide (III) had a retention time of 13.5 min. On evaporation of the solvent it crystallized and then it was recrystallized from ether-hexane. m.p.: 58°–58.5° C.

b.

5-Alkylthio-1,2-dihydro-3H-pyrrolo[1,2-a]pyrrole-1-carbonitriles

Similarly, using the procedure of Preparation 1.a. but substituting dimethylsulfide for dialkylsulfide other 5-alkylthio-1,2-dihydro-3H-pyrrolo[1,2-a]pyrrole-1-carbonitriles are prepared.

PREPARATION 2

Preparation of methyl-6-alkylthio-1,2-dihydro-3H-pyrrolo[1,2-a]pyrrole-1-carboxylates a. 5-Methylthio-1,2-dihydro-3H pyrrolo[1,2-a]pyrrole-1-carboxylic acid (IV) and 5-methylthio-1,2-dihydro-3H-pyrrolo[1,2-a]pyrrole methyl ester (V)

A solution of 85% potassium hydroxide (53.0 g, 0.805 mol) in 500 ml water was added to a solution of the methylsulfide (III) (53.0 g, 0.29 mol) and the resulting solution was heated at reflux temperature for 8 h. The alcohol was removed in vacuo and the aqueous residue was extracted twice with 300 ml of ether. The aqueous phase was acidified with 10% hydrochloric acid to ca. pH 3 and the product was extracted into ethyl acetate. The extract was washed 3 times with 100 ml of water, dried over sodium sulfate and evaporated in vacuo to provide compound (IV).

The residual carboxylic acid (IV) was dissolved in ether and an excess of a solution of diazomethane in ether was added. When the reaction was completed the solvent was removed in vacuo to give the oily methyl 5-methylthio-1,2-dihydro-3H-pyrrolo[1,2-a]pyrrole-1-carboxylate (V) in 80% yield which has the following physical data.

U.V. 222, 252 nm (6170, 7240),

I.R. ($CHCl_3$), 1742 $cm^{-1}$,

N.M.R. (CDCl$_3$), 2.28 (s, 3H), 2.83 (m, 2H), 3.80 (s, 3H), 4.10 (m, 3H), 6.00 (d, 1H, J=4 Hz), 6.36 (d, 1H, J=4 Hz),
M.S. 211 (M+).

b. 5-Alkylthio-1,2-dihydro-3H-pyrrolo[1,2-a]pyrrole-1-carboxylic acids and methyl 5-alkylthio-1,2-dihydro-3H-pyrrolo[1,2-a]pyrrole-1-carboxylates Similarly, using the procedure of Preparation 2.a. but substituting methylsulfide by alkylsulfide obtained by the procedure of Preparation 1.b, 5-alkylthio-1,2-dihydro-3H-pyrrolo[1,2-a]pyrrole-1-carboxylic acids and methyl 5-alkylthio-1,2-dihydro-3H-pyrrolo[1,2-a]pyrrole-1-carboxylates are prepared.

PREPARATION 3

Preparation of methyl-6-alkylthio-1,2-dihydro-3H-pyrrolo[1,2-a]pyrrole-1-carboxylates a. Methyl 6-methylthio-1,2-dihydro-3H-pyrrolo[1,2-a]pyrrole-1-carboxylate (VI)

To a solution of 3.0 g of the methyl ester (V) in 30 ml of dichloromethane was added 28 ml of trifluoroacetic acid and the solution was stirred at room temperature for 0.5 hour. A saturated solution of sodium bicarbonate in water was added to neutralize the acid, the organic phase was separated, dried over sodium sulfate and evaporated in vacuo. The residue was dissolved in dichloromethane and passed over a short column of neutral alumina (30 g) and evaporated to yield 75% of compound (VI) as an oil.

b. Methyl-6-alkylthio-1,2-dihydro-3H-pyrrolo[1,2-a]pyrrole-1-carboxylates

Similarly, using the procedure of Preparation 3.a. but substituting methyl ester by alkyl esters obtained by the procedure of Preparation 2.b, methyl-6-alkylthio-1,2-dihydro-3H-pyrrolo-[1,2-a]pyrrole-1-carboxylates are prepared.

PREPARATION 4

Preparation of 5-alkylsulfinyl-1,2-dihydro-3H-pyrrolo[1,2-a]pyrrole-1-carbonitriles a. 5-Methylsulfinyl-1,2-dihydro-3H-pyrrolo[1,2-a]pyrrole-1-carbonitrile (VIII)

A solution of 1.20 g of the methylsulfide (III) in 30 ml of methanol was cooled to 0° and 1.58 g of sodium periodate dissolved in 30 ml of water was added with stirring over a 20 min. period. The cooling bath was then removed and the reaction was stirred at room temperature for 3 hours. The methanol was removed in vacuo and the residue was extracted twice with 150 ml of dichloromethane. The aqueous phase was diluted with water, saturated with sodium chloride and then extracted again with 150 ml of dichloromethane. The combined extracts were dried over sodium sulfate and evaporated in vacuo to give 1.27 g of sulfoxide as an oil (VIII) which was pure enough to be used directly in the synthesis of 6-methylsulfinyl compound (IX). Compound (VIII) had the following N.M.R. spectral absorptions (CDCl$_3$): 2.83–3.17 (m, 2H), 2.93 (s, 3H), 3.94–4.57 (m, 3H, N), 5.32 (m, 1H), 6.58, 6.60 (doublets, total 1H, J=4 Hz).

b. 5-Alkylsulfinyl-1,2-dihydro-3H-pyrrolo[1,2-a]pyrrole-1-carbonitriles

Similarly, using the procedure of Preparation 4.a. but substituting a methylsulfide of alkylsulfide obtained by procedure of preparation 1.b., 5-alkylsulfinyl-1,2-dihydro-3H-pyrrolo[1,2-a]pyrrole-1-carbonitriles are prepared.

PREPARATION 5

Preparation of 6-alkylsulfinyl-1,2-dihydro-3H-pyrrolo[1,2-a]pyrrole-1-carbonitriles a. 6-Methylsulfinyl-1,2-dihydro-3H-pyrrolo[1,2-a]pyrrole-1-carbonitrile (IX)

A solution of 1.05 g of the methylsulfoxide (VIII) in 20 ml of dry dichloromethane containing 10 ml of trifluoroacetic acid was left at room temperature for 1 hour 50 min. The solution was diluted with 250 ml of benzene and then evaporated in vacuo. The dark colored oil so obtained was applied to a short column of silica gel (4 in.×1 in.). The column was eluted with dichloromethane (to remove non-polar impurities), then with ethyl acetate-triethylamine (95:5) (to remove colored material), and the product sulfoxide (IX) was eluted from the column with ethyl acetate-triethylamine (9:1) e.g. 1.02 g of the sulfoxide (IX) was obtained as an oil. It was used in the next preparation without further purification.

Repetition of the reaction commencing with 4.82 g of the sulfoxide mixture (VIII) gave the 4.27 g of isomeric sulfoxide mixture (IX).

Oil

N.M.R.: (CHCl$_3$), 2.79–3.21 (m, 2H), 2.81 (s, 3H), 3.88–4.57 (m, 3H), 6.47 (s, 1H), 7.12 (s, 1H).

b. 6-Alkylsulfinyl-1,2-dihydro-3H-pyrrolo[1,2-a]pyrrole-1-carbonitriles

Similarly, using the procedure of Preparation 5.a. but substituting a methylsulfoxide by alkylsulfoxide obtained in Preparation 4.b., 6-alkylsulfinyl-1,2-dihydro-3H-pyrrolo[1,2-a]-pyrrole-1-carbonitriles are obtained.

PREPARATION 6

Preparation of 6-alkylthio-1,2-dihydro-3H-pyrrolo[1,2-a]pyrrole-1-carbonitrile (X)

a. 6-Methylthio-1,2-dihydro-3H-pyrrolo[1,2-a]pyrrole-1-carbonitrile (X)

The reduction of the sulfoxide (IX) to the sulfide (X) was effected using the method of G.A. Olah et al, Synthesis, 137 (1978).

Powdered iodine (1 eq.) was added to a stirred solution of triphenylphosphine (1.15 eq.) in dry acetonitrile (10 ml/mmol of sulfoxide to be used) in a nitrogen atmosphere. The mixture was stirred until the iodine color was no longer present and a yellow colored suspension had formed. The sulfoxide (IX) (1 eq.) in dry acetonitrile (2.5 ml/mmol sulfoxide) was added in one portion. This was immediately followed by adding the solid powdered sodium iodide (2 eq.). The mixture was stirred and rapidly changed to a dark color. TLC showed that the reaction was complete after 1 min. After stirring for no more than 5 min. the solution was poured into a mixture of 5% sodium thiosulfate solution and ether. The mixture was shaken until the iodine color had disappeared, the ether phase was separated and washed with a 5% sodium bicarbonate solution. The ether solution was dried over sodium sulfate and evaporated in vacuo. The crude material was passed through a short column of silica gel (30 g/g of crude product) using dichloromethane. The excess triphenylphosphine came off with the solvent front and was followed almost immediately by the product compound (X). The sulfide (X) was obtained as an oil which was sufficiently pure to be used in the next step.

b.
6Alkylthio-1,2-dihydro-3H-pyrrolo[1,2-a]pyrrole-1-carbonitrile (X)

Similarly, alkylsulfoxides were reduced to alkylsulfides following the procedure of Preparation 6.a.

EXAMPLE 1

Methyl 5-aroyl-6-alkylthio-1,2-dihydro-3H-pyrrolo[1,2-a]-pyrrole-1-carboxylates a.
Methyl-5-aroyl-6-methylthio-1,2-dihydro-3H-pyrrolo[1,2-a]-pyrrole-1-carboxylates (VII)

This example illustrates a method, according to the invention, of preparing methyl esters of 5-aroyl-6-methylthio-1,2-dihydro-3H-pyrrolo[1,2-a]pyrrole-1-carboxylic acids.

The method described infra was used for the synthesis of all methyl esters. The Table I following the specific compounds which were synthesized shows the conditions used for each individual compound such as reaction time, amount (in eq.) of aroyl chloride used, the solvent from which the product is crystallized and yield in %.

The appropriate carboxylic acid chloride described specifically in Section II. A, B, C, D and E (for quantity see Table I) was added to a solution of 2.11 g (10 mmol) of the methyl ester (VI) of Preparation 3.a. in 120 ml of anhydrous toluene. The solution was heated at reflux temperature in nitrogen atmosphere for the times specified in Table I. The solvent was removed in vacuo and the residue was subjected to column chromatography on neutral alumina (Act. II, 10 g/g of crude material). The esters were eluted twice with hexane-ethyl acetate (95:5% v/v, then 90:10% v/v). The yields indicated in the Table I are based on compound (VI) as the starting material. The crystallization solvent specifies the solvent from which the compound was crystallized. The physical constants for the esters which were synthesized are listed after each compound.

b. Methyl 5-aroyl-6-alkylthio-1,2-dihydro-3H-pyrrolo[1,2-a]pyrrole-1-carboxylates (VII)

The same method as used in Section a. of this Example is used for the preparation of other methyl 5-aroyl-6-alkylthio-1,2-dihydro-3H-pyrrolo[1,2-a]pyrrole-1-carboxylates.

The appropriate carboxylic acid chloride described specifically in Section II.A, B, C, D and E is added to a solution of 2.11 g (10 mmol) of the alkyl ester (VI) of Preparation 3.b. in 120 ml of anhydrous toluene. The solution is heated at reflux temperature in nitrogen atmosphere for 1-72 hours, depending on the compound. The solvent is removed in vacuo and the residue is subjected to column chromatography on neutral alumina (Act. II, 10 g/g of crude material). The column is developed with hexane-ethyl acetate (95:5% v/v, then 90:10% v/v). The compound is crystallized from organic solvent or mixture thereof.

II. Synthesis of specific compounds

A. Synthesis of methyl 5-benzoyl-6-alkylthio-1,2-dihydro-3H-pyrrolo[1,2-a]pyrrol-1-carboxylates a. Synthesis of methyl 5-benzoyl-6-methylthio-1,2-dihydro-3H-pyrrolo[1,2-a]pyrrole-1-carboxylates The method of Section I.a. of this example for the synthesis of methyl 5-benzoyl-6-methylthio-1,2-dihydro-3H-pyrrolo[1,2-a]pyrrole-1-carboxylates wherein an appropriately substituted benzoyl chloride was used as the appropriate carboxylic acid chloride. Using this method the following compounds were prepared.

1. Methyl 5-(4-bromobenzoyl)-6-methylthio-1,2-dihydro-3H-pyrrolo[1,2-a]pyrrole-1-carboxylate M.P.: 136°–137° C. (methanol).

2. Methyl 5-(4-methylbenzoyl)-6-methylthio-1,2-dihydro-3H-pyrrolo[1,2-a]pyrrole-1-carboxylate M.P.: 122°–124° C. (methanol).

3. Methyl 5-(4-vinylbenzoyl)-6-methylthio-1,2dihydro-3H-pyrrolo[1,2-a]pyrrole-1-carboxylate M.P.: 120°–121° C. (dichloromethane-methanol).

4. Methyl 5-(4-ethylbenzoyl)-6-methylthio-1,2-dihydro-3H-pyrrolo[1,2-a]pyrrole-1-carboxylate
Oil.
U.V. 216, 261, 305 nm (14,100; 9550; 13,800).
I.R. (CHCl$_3$), 1739, 1600 cm$^{-1}$.
N.M.R. (CDCl$_3$), 1.16 (t, 3H, J=7.5 Hz), 2.30 (s, 3H), 2.75 (m, 4H), 3.66 (s, 3H), 4.26 (m, 3H), 6.11 (s, 1H), 7.28 (d, 2H, J=8), 7.66 (d, 2H, J=8 Hz).

5. Methyl 5-(4-ethoxybenzoyl)-6-methylthio-1,2-dihydro-3H-pyrrolo[1,2-a]pyrrole-1-carboxylate
Oil.
U.V. 215, 227, 307 nm (13,200; 13,500; 16,900).
I.R. (CHCl$_3$), 1742, 1600 cm$^{-1}$.
N.M.R. (CDCl$_3$), 1.45 (t, 3H, J=6 Hz), 2.30 (s, 3H), 2.81 (m, 2H), 3.60 (s, 3H), 4.16 (m, 5H), 6.10 (s, 1H), 6.96 (d, 2H, J=9 Hz), 7.73 (d, 2H, J=9 Hz).

6. Methyl 5-(4-i-propoxybenzoyl)-6-methylthio-1,2-dihydro-3H-pyrrolo[1,2-a]pyrrole-1-carboxylate
Oil.
U.V. 215, 218, 308 nm (13,200; 13,200; 17,000).
I.R. (CHCl$_3$), 1742, 1600 cm$^{-1}$.
N.M.R. (CDCl$_3$), 1.36 (d, 6H, J=6 Hz), 2.28 (s, 3H), 2.80 (m, 2H), 3.78 (s, 3H), 4.20 (m, 3H), 4.66 (sept. 1H, J=6 Hz), 6.10 (s, 1H), 6.93 (d, 2H, J=8 Hz), 7.71 (d, 2H, J=8 Hz).

7. Methyl 5-(4-methylthiobenzoyl)-6-methylthio-1,2-dihydro-3H-pyrrolo[1,2-a]pyrrole-1-carboxylate
Oil.
U.V. 215, 231(sh), 318 nm (14,500; 13,200; 19,100).
I.R. (CHCl$_3$), 1745, 1590 cm$^{-1}$.
N.M.R. (CDCl$_3$), 2.30 (s, 3H), 2.55 (s, 3H), 2.81 (m, 2H), 3.80 (s, 3H), 4.23 (m, 3H), 6.10 (s, 1H), 7.30 (d, 2H, J=8 Hz), 7.66 (d, 2H, J=8 Hz).

8. Methyl 5-(4-trifluoromethylbenzoyl)-6-methylthio-1,2-dihydro-3H-pyrrolo[1,2-a]-pyrrole-1-carboxylate
M.P.: 90°–92° C. (dichloromethane-methanol).

9. Methyl 5-(4-cyclohexylbenzoyl)-6-methylthio-1,2-dihydro-3H-pyrrolo[1,2-a]pyrrole-1-carboxylate
Oil.
U.V. 219, 263, 306(sh), 365 nm (12,300; 9,550; 12,600; 6,610).
I.R. (CHCl$_3$), 1739, 1603 cm$^{-1}$.
N.M.R. (CHCl$_3$), 1.60 (m, 11H), 2.28 (s, 3H), 2.80 (m, 2H), 3.80 (s, 3H), 4.21 (m, 3H), 6.10 (s, 1H), 7.28 (d, 2H, J=8 Hz), 7.56 (d, 2H, J=8 Hz).

10. Methyl 5-(4-n-propylbenzoyl)-6-methylthio-1,2-dihydro-3H-pyrrolo[1,2-a]pyrrole-1-carboxylate
Oil.
U.V. 223, 262, 308, 354 nm (11,800; 8,710; 12,900; 7,080).
I.R. (CHCl$_3$), 1730, 1600 cm$^{-1}$.
N.M.R. (CHCl$_3$), 0.95 (t, 3H, J=6 Hz), 1.68 (m, 2H), 2.30 (s, 3H), 2.76 (m, 2H), 3.98 (s, 3H), 4.23 (m, 3H), 6.14 (s, 1H), 7.30 (d, 2H, J=8 H), 7.66 (d, 2H, J=8 Hz).

11. Methyl 5-(4-cyclopropylbenzoyl)-6-methylthio-1,2-dihydro-3H-pyrrolo[1,2-a]pyrrole-1-carboxylate
M.P.: 94°–94° C. (ethyl acetate-hexane).

TABLE I

| Compound Formula (1) | R$_2$ | Reaction Time (h) | 5-benzoyl chloride (eq.) | Cryst. Solvent | Yield % |
|---|---|---|---|---|---|
| (1) | 4-Bromo | 22 | 2 | CH$_3$OH | 26 |
| (2) | 4-Methyl | 24 | 2.5 | CH$_3$OH | 31 |
| (3) | 4-Vinyl | 5 | 2.5 | CH$_3$OH | 17 |
| (4) | 4-Ethyl | 20 | 2 | oil | 36 |
| (5) | 4-Ethoxy | 48 | 2 | oil | 23 |
| (6) | 4-Propoxy | 58 | 2 | oil | 30 |
| (7) | 4-Methylthio | 24 | 2 | oil | 40 |
| (8) | 4-Trifluoromethyl | 3 | 2 | CH$_2$Cl$_2$—CH$_3$OH | 38 |
| (9) | 4-Cyclohexyl | 72 | 1.7 | oil | 15 |
| (10) | 4-N—Propyl | 48 | 2.75 | oil | 33 |
| (11) | 4-Cyclopropyl | 36 | 3 | EtOAc—Hexane | 35 | b. Methyl 5-benzoyl-6-alkylthio-1,2-dihydro-3H-pyrrole[1,2-a]pyrrole-1-carboxylates Similarly, in the same manner, methyl 5-benzoyl-6-alkylthio-1,2-dihydro-3H-pyrrolo[1,2-a]pyrrole-1-carboxylates are prepared.

B. Synthesis of methyl 5-(2-thenoyl)-6-alkylthio-1,2-dihydro-3H-pyrrolo[1,2-a]pyrrole-1-carboxylates or methyl-5-(3-thenoyl)-6-alkylthio-1,2-dihydro-3H-pyrrolo[1,2-a]-pyrrole-1-carboxylates The same method as outlined in Section I.b. of this example is used for the synthesis of methyl 5-(2-thenoyl)-6-alkylthio-1,2-dihydro-3H-pyrrolo[1,2-a]pyrrole-1-carboxylates or methyl 5-(3-thenoyl)-6-alkylthio-1,2-dihydro-3H-pyrrolo[1,2-a]-pyrrole-1-carboxylates. 2-Thenoyl or 3-thenoyl chlorides are used as the appropriate carboxylic acid chlorides.

C. Synthesis of methyl 5-(2-furoyl)-6-alkylthio-1,2-dihydro-3H-pyrrolo[1,2-a]pyrrole-1-carboxylates or methyl 5-(3-furoyl)-6-alkylthio-1,2-dihydro-3H-pyrrolo[1,2-a]-pyrrole-1-carboxylates The same method as outlined supra in Section I.b. of this example is used for the synthesis of methyl 5-(2-furoyl)-6-alkylthio-1,2-dihydro-3H-pyrrolo[1,2-a]-pyrrole-1-carboxylates or methyl 5-(3-furoyl)-6-alkylthio-1,2-dihydro-3H-pyrrolo[1,2-a]-pyrrole-1-carboxylates wherein 2-furoyl or 3-furoyl chloride, respectively, are used as appropriate carboxylic acid chlorides.

D. Synthesis of methyl 5-(2-pyrrolyl)-6-alkylthio-1,2-dihydro-3H-pyrrolo[1,2-a]pyrrole-1-carboxylates or methyl 5-(3-pyrrolyl)-6-alkylthio-1,2-dihydro-3H-pyrrolo[1,2-a]-pyrrole-1-carboxylates The same method as outlined supra in Section I.b. of this example is used for the synthesis of methyl 5-(2-pyrrolyl)-6-alkylthio-1,2-dihydro-3H-pyrrolo[1,2-a]-pyrrole-1-carboxylates or methyl 5-(3-pyrrolyl)-6-alkylthio--1,2-dihydro-3H-pyrrolo[1,2-a]-pyrrole-1-carboxylates wherein 2-pyrrole or 3-pyrrole carboxylic acid chlorides are used as appropriate carboxylic acid chlorides.

E. Synthesis of methyl 5-(N-alkyl-2-pyrrolyl)-6-alkylthio-1,2-dihydro-3H-pyrrolo[1,2-a]pyrrole-1-carboxylates or methyl 5-(N-alkyl-3-pyrrolyl)-6-alkylthio-1,2-dihydro-3H-pyrrolo[1,2-a]-pyrrole-1-carboxylates The same method as outlined supra in Section I.b. of this example is used for the synthesis of methyl 5-(N-alkyl-2-pyrrolyl)-6-alkylthio-1,2-dihydro-3H-pyrrolo[1,2-a]pyrrole-1-carboxylates or methyl 5-(N-alkyl-3-pyrrolyl)-6-alkylthio-1,2-dihydro-3H-pyrrolo[1,2-a]-pyrrole-1-carboxylates wherein N-alkyl-2-pyrrolyl or N-alkyl-3-pyrrole carboxylic acid chlorides respectively, are used as appropriate carboxylic acid chlorides.

EXAMPLE 2

I.

5-Aroyl-6-Alkylthio-1,2-dihydro-3H-pyrrolo[1,2-A]-pyrrole-1-carbonitriles (XI)

a.

5-Aroyl-6-methylthio-1,2-dihydro-3H-pyrrolo[1,2-a]pyrrole-1-carbonitriles (XI)

This example illustrates a method, according to the invention, of preparing carbonitriles of 5-aroyl-6-methylthio-1,2-dihydro-3H-pyrrolo[1,2-a]-pyrrole.

The method as described infra was used, with small variations pointed out after specific compounds, for the synthesis of all carbonitriles. Table II shows the specific conditions used for each individual compound such as reaction time, amount of sulfide (in g) used, amount of aroyl chloride (in g) used and yield in %.

A solution of the crude sulfide (X) of Preparation 6 (for quantities see Table 2) in 25 ml of xylene containing the appropriate acid chloride (for quantities see Table II) was heated at reflux temperature for the reaction times specified in Table II. When the reaction was complete as shown by TLC [ethyl acetate-hexane (3:7)], 25 ml of methanol was added to esterify the excess acid chloride and then the mixture was evaporated in vacuo.

Compounds were purified by the following procedure. The residue was slurried with an appropriate amount of Fluka Act II neutral alumina and the slurry was placed on top of a short column of the same stationary phase. The products were eluted with an appropriate solvent system. The purification procedures vary for individual compounds and are described under each compound.

The solvent systems used for elution of the individual compounds and obtained physical data are listed following each individual compounds.

b. 5-Aroyl-6-alkylthio-1,2-dihydro-3H-pyrrolo [1,2-a]-pyrrole-1-carbonitriles (XI)

5-Aroyl-6-alkylthio-1,2-dihydro-3H-pyrrolo-[1,2-a]-pyrrole-1-carbonitriles are prepared similarly.

A solution of the crude alkylsulfide (X) of Preparation 6 in 25 ml of xylene containing the appropriate acid chloride is heated at reflux temperature for 1–35 hours, depending on the compound. When the reaction is complete as shown by TLC [ethyl acetate-hexane (3:7)], 25 ml of methanol is added to esterify the excess acid chloride. The mixture is then evaporated in vacuo. Compounds are purified by the following procedure. The residue is slurried with an appropriate amount of Fluka Act II neutral alumina and slurry is placed on top of a short column of the same stationary phase. The product is then eluted with an appropriate solvent system as described below.

II. Synthesis of specific compounds

A. Synthesis of 5-benzoyl-6-alkylthio-1,2-dihydro-3H-pyrrolo[1,2-a]pyrrole-1-carbonitriles a. Synthesis of 5-benzoyl-6-methylthio-1,2-dihydro-3H-pyrrolo[1,2-a]pyrrole-1-carbonitriles The method of Section I of this example was used for the synthesis of 5-benzoyl-6-methylthio-1,2-dihydro-3H-pyrrolo[1,2-a]pyrrole-1-carbonitriles where appropriate substituted benzoyl chloride was introduced as the appropriate carboxylic acid chloride. Using this method with small variations specified under each compound the following compounds were prepared.

12. 5-Benzoyl-6-methylthio-1,2-dihydro-3H-pyrrolo-[1,2-a]pyrrole-1-carbonitrile

The crude product obtained by method of Example 2.I.a. was purified by slurrying the said product with 20 g of neutral alumina and then placing it on top of a column of 50 g of the same stationary phase. To remove the methyl ester of the carboxylic acid derived from the excess acid chloride, the column was eluted with hexane, then with ethyl acetate-hexane (1:99%, v/v), ethyl acetate-hexane (2:98%, v/v), and finally with dichloromethane to remove the product, compound (12). This material was further purified by preparative TLC on silica gel [ethyl acetate-hexane (3:7)]. Compound (12) was crystallized from dichloromethane-ether.

M.P.: 90°–91°

13. 5-(4-fluorobenzoyl)-6-methylthio-1,2-dihydro-3H-pyrrolo[1,2-a]pyrrole-1-carbonitrile The crude product obtained by method of Example 2.I.a. was slurried with 20 g of neutral Act II alumina and placed on top of a column of 50 g of this stationary phase. Elution was then effected with hexane, ethyl acetate-hexane (1:99%, v/v), ethyl acetate-hexane (2:98%, v/v), ethyl acetate-hexane (3:97, v/v) and dichloromethane. Compound (13) was crystallized from dichloromethane-ether.

M.P.: 127°–127.5° C.

14. 5-(4-chlorobenzoyl)-6-methylthio-1,2-dihydro-3H-pyrrolo[1,2-a]pyrrole-1-carbonitrile For purification of this compound, the purification procedure for compound (13) of Example 2.II.A.a.13. was used.

M.P.: 160.5°–161° C. (dichloromethane-ether).

15. 5-(4-methoxybenzoyl)-6-methylthio-1,2-dihydro-3H-pyrrolo[1,2-a]pyrrole-1-carbonitrile.

The crude product obtained by method of Example 2.I.a. was slurried with 30 g of alumina and placed on top of a column of 50 g of the same stationary phase. The column was developed with hexane, ethyl acetate-hexane (2:98), ethyl acetate-hexane (3:97), ethyl acetate-hexane (4:96) and dichloromethane. The product thus obtained was rechromatographed on silica gel (50 g). The column was developed with dichloromethane-hexane (1:1), dichloroethane-hexane (3:1), dichloromethane, and then ether. The first three solvent systems removed a red colored material, the last eluted the product (15). Compound (15) was crystallized from dichloromethane-ether.

M.P.: 137.5°–139° C.

TABLE II

| Compound formula (1) | $R_2$ | Reaction Time (h) | Sulfide (g) | Benzoyl Chloride (g) | Yield % |
|---|---|---|---|---|---|
| (12) | 4-Hydrogen | 20 | 0.687 | 1.80 | 84 |
| (13) | 4-Fluoro | 8 | 1.062 | 2.85 | 82 |
| (14) | 4-Chloro | 8 | 1.062 | 3.00 | 82 |
| (15) | 4-Methoxy | 31 | 1.062 | 5.00 | 64 | b. 5-Benzoyl-6-alkylthio-1,2-dihydro-3H-pyrrolo[1,2-a]pyrrole-1-carbonitriles

Similarly, in the same manner, 5-benzoyl-6-alkylthio-1,2-dihydro-3H-pyrrolo[1,2-a]pyrrole-1-carbonitriles are prepared.

B. Synthesis of 5-(2-thenoyl)-6-alkylthio-1,2-dihydro-3H-pyrrolo[1,2-a]pyrrole-1-carbonitriles or 5-(3-thenoyl)-6-alkylthio-3-thenoyl-1,2-dihydro-3H-pyrrolo[1,2-a]pyrrole-1-carbonitriles The same method as outlined in Section I.b. of this example is used for the synthesis of 5-(2-thenoyl)-6-alkylthio-1,2-dihydro-3H-pyrrolo[1,2-a]pyrrole-1-carbonitriles or 5-(3-thenoyl)-6-alkylthio-1,2-dihydro-3H-pyrrolo[1,2-a]-pyrrole-1-carbonitriles. 2-Thenoyl or 3-thenoyl chlorides are used as the appropriate carboxylic acid chloride.

C. Synthesis of 5-(2-furoyl)-6-alkylthio-1,2-dihydro-3H-pyrrolo[1,2-a]pyrrole-1-carbonitrile or 5-(3-furoyl)-6-alkylthio-1,2-dihydro-3H-pyrrolo[1,2-a]pyrrole-1-carbonitrile The same method as outlined supra in Section I.b. of this example is used for the synthesis of 5-(2-furoyl)-6-alkylthio-1,2-dihydro-3H-pyrrolo[1,2-a]-pyrrole-1-carbonitrile or 5-(3-furoyl)-6-alkylthio-1,2-dihydro-3H-pyrrolo[1,2-a]-pyrrole-1-carbonitrile wherein 2-furoyl or 3-furoyl chlorides, respectively, are used as appropriate carboxylic acid chlorides.

D. Synthesis of methyl 5-(2-pyrrolyl)-6-alkylthio-1,2-dihydro-3H-pyrrolo[1,2-a]pyrrole-1,2-dihydro-3H-pyrrolo[1,2-a]pyrrole-1-carbonitriles The same method as outlined supra in Section I.b. of this example is used for the synthesis of 5-(2-pyrrolyl)-6-alkylthio-1,2-dihydro-3H-pyrrolo[1,2-a]pyrrole-1-carbonitriles or 5-(3-pyrrolyl)-6-alkylthio 1,2-dihydro-3H-pyrrolo[1,2-a]pyrrole-1-carbonitriles wherein 2-pyrrole or 3-pyrrole carboxylic acid chlorides, respectively, are used as appropriate carboxylic acid chlorides.

E. Synthesis of methyl 5-(N-alkyl-2-pyrrolyl)-6-alkylthio-1,2-dihydro-3H-pyrrolo[1,2-a]pyrrole-1-carbonitriles or methyl 5-(N-alkyl-3-pyrrolyl)-6-alkylthio-1,2-dihydro-3H-pyrrolo[1,2-a]pyrrole-1-carbonitriles The same method as outlined supra in Section I.b. of this example is used for the synthesis of methyl 5-(N-alkyl-2-pyrrolyl)-6-alkylthio-1,2-dihydro-3H-pyrrolo-[1,2-a]pyrrole-1-carbonitriles or methyl 5-(N-alkyl-3-pyrrolyl)-6-alkylthio-1,2-dihydro-3H-pyrrolo[1,2-a]-pyrrole-1-cabronitriles wherein alkyl-2-pyrrole or alkyl-3-pyrrole carboxylic acid chlorides, respectively, are used as appropriate carboxylic acid chlorides.

EXAMPLE 3

I. Synthesis of 5-aroyl-6-alkylthio-1,2-dihydro-3H-pyrrolo[1,2-a]pyrrole-1-carboxylic acids (1) or (2) by hydrolysis of the carbonitriles (XI)

a. Synthesis of 5-aroyl-6-methylthio-1,2-dihydro-3H-pyrrolo[1,2-a]pyrrole-1-carboxylic acids (1) or (2) by hydrolysis of the carbonitriles (XI)

This example illustrates a method, according to the invention, of preparing 5-aroyl-6-methylthio-1,2-dihydro-3H-pyrrolo[1,2-a]-pyrrole-1-carboxylic acids from 5-aroyl-6-methylthio-1,2-dihydro-3H-pyrrolo[1,2-a]pyrrole carbonitriles.

The method, as described infra, was used for preparation of specific carboxylic acids as described hereinafter. The specific conditions used for the preparation of each individual compound are summarized in Table III which follows the description of specific compounds.

A solution of the carbonitrile (XI) (1 eq.) in 30 ml of 96% ethanol containing sodium hydroxide (for amount see Table III) and 10 ml of water was heated at reflux temperature for the times specified in Table III. The ethanol was removed in vacuo and the residual aqueous phase was diluted with water and extracted with ether. The aqueous alkaline phase was made acidic with 1N hydrochloric acid, the product was extracted into ethyl acetate. The extract was dried over sodium sulfate, and evaporated in vacuo. The residual solid was crystallized from ethyl acetate or solvent specified in Table III. The physical constants of the carboxylic acids follow the individual compounds.

b. Synthesis of 5-aroyl-6-alkylthio-1,2-dihydro-3H-pyrrolo[1,2-a]pyrrole-1-carboxylic acids (1) or (2) by hydrolysis of the carbonitriles (XI)

5-Aroyl-6-alkylthio-1,2-dihydro-3H-pyrrolo[1,2-a]-pyrrole-1-carboxylic acids are prepared similarly.

A solution of the carbonitrile (XI) (1 eq.) in 30 ml of 96% ethanol containing sodium hydroxide and 10 ml of water is heated at reflux temperature for 1-16 hours, depending on compound. The ethanol was removed in vacuo and the residual aqueous phase is diluted with water and extracted with ether. The aqueous alkaline phase is made acidic with 1N hydrochloric acid and the product is extracted into ethyl acetate. The extract is dried over sodium sulfate, and evaporated in vacuo. The residual solid is crystallized from organic solvent or mixture thereof.

II. The synthesis of specific compounds

A. Synthesis of 5-benzoyl-6-alkylthio-1,2-dihydro-3H-pyrrolo[1,2-a]pyrrole-1-carboxylic acids a. Synthesis of 5-benzoyl-6-methylthio-1,2-dihyro-3H-pyrrolo[1,2-a]pyrrole-1-carboxylic acids 5-Benzoyl-6-methylthio-1,2-dihydro-3H-pyrrolo[1,2-a]pyrrole-1-carboxylic acids are prepared by following the procedure of Section I.a. of this Example. An appropriately substituted benzoyl chloride group was introduced as the appropriate carboxylic acid chloride.

16.  5-benzoyl-6-methylthio-1,2-dihydro-3H-pyrrolo[1,2-a]-pyrrole-1-carboxylic acid 5-benzoyl-6-methylthio-1,2-dihydro-3H-pyrrolo[1,2-a]-pyrrole-1-carboxylic acid (16) was prepared following the procedure of Example 3.I.a. and using as a starting carbonitrile the solution of 5-benzoyl-6-methylthio-1,2-dihydro-3H-pyrrolo[1,2-a]pyrrole-1-carbonitrile (12) from Example 2.II.A.a.12. The compound (16) was crystallized from ethyl acetate.

M.P.: 191°–192° C.

17.  5-(4-fluorobenzoyl)-6-methylthio-1,2-dihydro-3H-pyrrolo[1,2-a]pyrrole-1-carboxylic acid 5-(4-fluorobenzoyl)-6-methylthio-1,2-dihydro-3H-pyrrolo[1,2-a]pyrrole-1-carboxylic acid (17) was prepared following the procedure of Example 3.I.a. and using as a starting carbonitrile the solution of carbonitrile (13) 5-(4-fluorobenzoyl)-6-methylthio-1,2-dihydro-3H-pyrrolo-[1,2-a]pyrrole-1-carbonitrile from Example 2.II.A.a.13. Compound (17) was crystallized from ethyl acetate.

M.P.: 201°–202° C.

18.  5-(4-chlorobenzoyl)-6-methylthio-1,2-dihydro-3H-pyrrolo[1,2-a]pyrrole-1-carboxylic acid 5-(4-chlorobenzoyl)-6-methylthio-1,2-dihydro-3H-pyrrolo[1,2-a]pyrrole-1-carboxylic acid (18) was prepared following the procedure of Example 3.I.a. and using as a starting solution the carbonitrile (14) 5-(4-chlorobenzoyl)-6-methylthio-1,2-dihydro-3H-pyrrolo-1,2-a]pyrrole-1-carbonitrile of Example 2.II.A.a.14. Compound (18) was crystallized from ethyl acetate.

M.P.: 200.5°–201° C.

19.  5-(4-methoxybenzoyl)-6-methylthio-1,2-dihydro-3H-pyrrolo[1,2-a]pyrrole-1-carboxylic acid (19)

5-(4-methoxybenzoyl)-6-methylthio-1,2-dihydro-3H-pyrrolo[1,2-a]pyrrole-1-carboxylic acid (19) was prepared following the procedure of Example 3.I.a. and using as a starting solution the carbonitrile (15) 5-(4-methoxybenzoyl)-6-methylthio-1,2-dihydro-3H-pyrrolo-[1,2-a]pyrrole-1-carbonitrile of Example 2.II.A.a.15. Compound (19) was crystallized from ethyl acetate.

M.P.: 197°–198° C.

TABLE III

| Compound | R₂ | NaOH (equiv.) | Reaction Time (h) | Cryst. Solvent | Yield % |
|---|---|---|---|---|---|
| (16) | 4-Hydrogen | 3.9 | 8 | EtOAc | 77 |
| (17) | 4-Fluoro | 4 | 14.5 | EtOAc | 82 |
| (18) | 4-Chloro | 4.3 | 5 | EtOAc | 81 |
| (19) | 4-Methoxy | 4.7 | 8.5 | EtOAc | 78 | b.
5-Benzoyl-6-alkylthio-1,2-dihydro-3H-pyrrolo-[1,2-a]pyrrole-1-carboxylic acid Similarly, in the same manner, 5-benzoyl-6-alkylthio-1,2-dihydro-3H-pyrrolo[1,2-a]pyrrole-1-carboxylic acid are prepared.

B. Synthesis of 5-(2-thenoyl)-6-alkylthio-1,2-dihydro-3H-pyrrolo[1,2-a]pyrrole-1-carboxylic acid or 5-(3-thenoyl)-6-alkylthio-3-thenoyl-1,2-dihydro-3H-pyrrolo[1,2-a]pyrrole-1-carboxylic acid Similarly, using the method of Example 3.I.b., but substituting aroyl nitrile (XI) by 2- or 3-thenoyl nitriles of Example 2.II.B., 5-(2-thenoyl)-6-alkylthio-1,2-dihydro-3H-pyrrolo[1,2-a]pyrrole-1-carboxylic acid or 5-(3-thenoyl)-6-alkylthio-1,2-dihydro-3H-pyrrolo[1,2-a]-pyrrole-1-carboxylic acid are prepared.

C. Synthesis of 5-(2-furoyl)-6-alkylthio-1,2-dihydro-3H-pyrrolo[1,2-a]pyrrole-1-carboxylic acid or 5-(3-furoyl)-6-alkylthio-1,2-dihydro-3H-pyrrolo[1,2-a]pyrrole-1-carboxylic acid Similarly, using the method of Example 3.I.b. but substituting aroyl nitrile (XI) by 2- or 3- furoyl nitriles of Example 2.II.C., 5-(2- or 3- furoyl)-6-alkylthio-1,2-dihydro-3H-pyrrolo[1,2-a]pyrrole-1-carboxylic acids are prepared.

D. Synthesis of 5-(2-pyrrolyl)-6-alkylthio-1,2-dihydro-3H-pyrrolo[1,2-a]pyrrole-1-carboxylic acid or 5-(3-pyrrolyl)-6-alkylthio-1,2-dihydro-3H-pyrrolo[1,2-a]pyrrole-1-carboxylic acid Similarly, using the method of Example 3.I.b. but substituting aroyl nitrile (XI) by 2- or 3-pyrrole nitriles of Example 2.II.D., 5-(2-pyrrolyl)-6-alkylthio-1,2-dihydro-3H-pyrrolo[1,2-a]pyrrole-1-carboxylic acid or 5-(3-pyrrolyl)-6-alkylthio-1,2-dihydro-3H-pyrrolo-[1,2-a]pyrrole-1-carboxylic acid are prepared.

E. Synthesis of 5-(N-alkyl-2-pyrrolyl)-6-alkylthio-1,2-dihydro-3H-pyrrolo[1,2-a]pyrrole-1-carboxylic acid or 5-(N-alkyl-3-pyrrolyl)-6-alkylthio-1,2-dihydro-3H-pyrrolo[1,2-a]pyrrole-1-carboxylic acid Similarly, using the method of Example 3.I.b. but substituting aroyl nitrile (XI) by N-alkyl-2 or 3-pyrrole nitriles of Example 2.II.E., 5-(N-alkyl-2-pyrrolyl)-6-alkylthio-1,2-dihydro-3H-pyrrolo[1,2-a]-pyrrole-1-carboxylic acid or 5-(N-alkyl-3-pyrrolyl)-6-alkylthio-1,2-dihydro-3H-pyrrolo[1,2-a]pyrrole-1-carboxylic acid are prepared.

EXAMPLE 4

I. Synthesis of 5-aroyl-6-alkylthio-1,2-dihydro-3H-pyrrolo[1,2-a]pyrrole-1-carboxylic acid by hydrolysis of methyl ester (VII)

a. Synthesis of 5-aroyl-6-methylthio-1,2-dihydro-3H-pyrrolo[1,2-a]pyrrole-1-carboxylic acid by hydrolysis of methyl ester (VII)

This example illustrates a method, according to the invention, of preparing 5-aroyl-6-methylthio-1,2-dihydro-3H-pyrrolo[1,2-a]pyrrole carboxylic acids from methyl 5-aroyl-6-methylthio-1,2-dihydro-3H-pyrrolo[1,2-a]pyrrole carboxylates.

The method, as described infra, is used for the synthesis of all carboxylic acids which are listed in Section II of this Example. Table (IV) which follows the individual compounds shows the specific conditions used for each individual compound.

To a solution of 10 mmol of the ester (VII), prepared according to procedure of Example 1.I.a. in 60 ml of methanol was added a solution of sodium hydroxide (for amount see Table IV) in 60 ml of water. The resulting solution was stirred at room temperature for the time period specified in Table IV. The methanol was removed in vacuo and the aqueous residue was extracted with with 50 ml of ether. The aqueous alkaline phase was made acidic with 10% hydrochloric acid and the product was extracted into ethyl acetate. The extract was washed with water, dried over sodium sulfate and evaporated in vacuo. The yields, solvents of crystallization, reaction times and amounts of sodium hydroxide used for these individual compounds are given in Table IV. The physical constants for the carboxylic acids are listed following the individual compounds.

b. Synthesis of 5-aroyl-6-alkylthio-1,2-dihydro-3H-pyrrolo[1,2-a]pyrrole-1-carboxylic acid—by hydrolysis of methyl esters (VII)

5-Aroyl-6-alkylthio-1,2-dihydro-3H-pyrrolo-[1,2-a]-pyrrole-1-carboxylic acids are prepared similarly.

To a solution of 10 mmol. of the alkylester (VII), prepared according to procedure of Example 1.I.b. in 60 ml of methanol is added a solution of sodium hydroxide in 60 ml of water. The resulting solution is stirred at room temperature for 1-20 hours, depending on compound. The methanol is removed in vacuo and the aqueous residue is extracted with with 50 ml of ether. The aqueous alkaline phase is made acidic with 10% hydrochloric acid and the product is extracted into ethyl acetate. The extract is washed with water, dried over sodium sulfate and evaporated in vacuo. The compound is crystallized from organic solvent or mixture thereof.

II. Synthesis of specific compounds

A. Synthesis of 5-benzoyl-6-alkylthio-1,2-dihydro-3H-pyrrolo[1,2-a]pyrrole-1-carboxylic acid a. Synthesis of 5-benzoyl-6-methylthio-1,2-dihydro-3H-pyrrolo[1,2-a]pyrrole-1-carboxylic acid 5-Benzoyl-6-methylthio-1,2-dihydro-3H-pyrrolo[1,2-a]pyrrole-1-carboxylic acids are prepared by following the procedure of Section I.a. of this Example.

20. 5 (4-bromobenzoyl)-6-methylthio-1,2-dihydro-3H-(4-pyrrolo[1,2-a]pyrrole-1-carboxylic acid. M.P.: 204°-205° C. (acetone-ether).
21. 5-(4-methylbenzoyl)-6-methylthio-1,2-dihydro-3H-pyrrolo[1,2-a]pyrrole-1-carboxylic acid. M.P.: 182°-183° C. (ethyl acetate-ether).
22. 5-(4-vinylbenzoyl)-6-methylthio-1,2-dihydro-3H-pyrrolo[1,2-a]pyrrole-1-carboxylic acid. M.P.: 182°-183° C. (ethyl acetate).
23. 5-(4-ethylbenzoyl)-6-methylthio-1,2-dihydro-3H-pyrrolo[1,2-a]pyrrole-1-carboxylic acid. M.P.: 164°-166° C. (ethyl acetate-ether).
24. 5-(4-ethoxybenzoyl)-6-methylthio-1,2-dihydro-3H-pyrrolo[1,2-a]pyrrole-1-carboxylic acid M.P.: 167°-168° C. (ethyl acetate-ether).
25. 5-(4-i-propoxybenzoyl)-6-methylthio-1,2-dihydro-3H-pyrrolo[1,2-a]pyrrole-1-carboxylic acid. M.P.: 192°-193° C. (methanol).
26. 5-(4-methylthiobenzoyl)-6-methylthio-1,2-dihydro-3H-pyrrolo[1,2-a]pyrrole-1-carboxylic acid. M.P.: 185°-187° C. (ethyl acetate-ether).
27. 5-(4-trifluoromethylbenzoyl)-6-methylthio-1,2-dihydro-3H-pyrrolo[1,2-a]pyrrole-1-carboxylic acid. M.P.: 210°-211° C. (ethyl acetate-ether).
28. 5-(4-cyclohexylbenzoyl)-6-methylthio-1,2-dihydro-3H-pyrrolo[1,2-a]pyrrole-1-carboxylic acid. M.P.: 175°-176° C. (ethyl acetate-hexane).
29. 5-(4-propylbenzoyl)-6-methylthio-1,2-dihydro-3H-pyrrolo[1,2-a]pyrrole-1-carboxylic acid. M.P.: 160°-161° C. (ethyl acetate-ether).
30. 5-(4-cyclopropylbenzoyl)-6-methylthio-1,2-dihydro-3H-pyrrolo[1,2-a]pyrrole-1-carboxylic acid. M.P.: 186°-187° C. (ethyl acetate).

TABLE IV

| Compound formula (1) | $R_2$ | NaOH (equiv.) | Reaction Time (h) | Cryst. Solvent | Yield % |
|---|---|---|---|---|---|
| (20) | 4-Bromo | 2 | 5 | $Me_2CO-Et_2O$ | 80 |
| (21) | 4-Methyl | 2 | 3 | $EtOAc-Et_2O$ | 90 |
| (22) | 4-Vinyl | 2 | 5 | EtOAc | 52 |
| (23) | 4-Ethyl | 2 | 1 | $EtOAc-Et_2O$ | 50 |
| (24) | 4-Ethoxy | 2 | 18 | $EtOAc-Et_2O$ | 84 |
| (25) | 4-Propoxy | 2 | 18 | $EtOAc-MeOH$ | 71 |
| (26) | 4-Methylthio | 2 | 1 | $EtOAc-Et_2O$ | 50 |
| (27) | 4-Trifluoromethyl | 2.4 | 2 | $EtOAc-Et_2O$ | 58 |
| (28) | 4-Cyclohexyl | 2.25 | 2 | $EtOAc-Et_2O$ | 69 |
| (29) | 4-N—propyl | 2.25 | 2 | $EtOAc-Et_2O$ | 86 |
| (30) | 4-Cyclopropyl | 2 | 1.5 | EtOAc | 86 | b.
5-Benzoyl-6-alkylthio-1,2-dihydro-3H-pyrrolo-[1,2-a]pyrrole-1-carboxylic acid Similarly, in the same manner, 5-benzoyl-6-alkylthio-1,2-dihydro-3H-pyrrolo[1,2-a]pyrrole-1-carboxylic acid are prepared.

B. Synthesis of
5-(2-thenoyl)-6-alkylthio-1,2-dihydro-3H-pyrrolo[1,2-a]pyrrole-1-carboxylic acid or
5-(3-thenoyl)-6-alkylthio-1,2-dihydro-3H-pyrrolo[1,2-a]pyrrole-1-carboxylic acid Alternatively to the procedure of Example 3.II.B., by using the method of Example 4.I.b. but substituting the aroyl ester (VII) by 2- or 3-thenoyl methyl esters of Example 1.II.B., 5-(2-thenoyl)-6-alkylthio-1,2-dihydro-3H-pyrrolo[1,2-a]pyrrole-1-carboxylic acid or 5-(3-thenoyl)-6-alkylthio-1,2-dihydro-3H-pyrrolo[1,2-a]-pyrrole-1-carboxylic acid are prepared.

C. Synthesis of 5-(2-furoyl)-6-alkylthio-1,2-dihydro-3H-pyrrolo[1,2-a]pyrrole-1-carboxylic acid or 5-(3-furoyl)-6-alkylthio-1,2-dihydro-3H-pyrrolo[1,2-a]pyrrole-1-carboxylic acid Alternatively to the procedure of Example 3.II.C. by using the method of Example 4.I.b. but substituting the aroyl ester (VII) by 2- or 3-furoyl methyl esters of Example 1.II.C., 5-(2- or 3- furoyl)-6-alkylthio-1,2-dihydro-3H-pyrrolo[1,2-a]pyrrole-1-carboxylic acids are prepared.

D. Synthesis of
5-(2-pyrrolyl)-6-alkylthio-1,2-dihydro-3H-pyrrolo[1,2-a]pyrrole-1-carboxylic acid or
5-(3-pyrrolyl)-6-alkylthio-1,2-dihydro-3H-pyrrolo[1,2-a]pyrrole-1-carboxylic acid Alternatively to the procedure of Example 3.11.D., by using the method of Example 4.I.b., but substituting the aroyl ester (VII) by 2- or 3-pyrrolyl methyl esters of Example 1.II.D., 5-(2-pyrrolyl)-6-alkylthio-1,2-dihydro-H-pyrrolo[1,2-a]pyrrole-1-carboxylic acid or 5-(3-pyrrolyl)-6-alkylthio-1,2-dihydro-3H-pyrrolo-[1,2-a]pyrrole-1-carboxylic acid are prepared.

E. Synthesis of
5-(N-alkyl-2-pyrrolyl)-6-alkylthio-1,2-dihydro-3H-pyrrolo[1,2-a]pyrrole-1-carboxylic acid or
5-(N-alkyl-3-pyrrolyl)-6-alkylthio-1,2-dihydro-3H-pyrrolo[1,2-a]pyrrole-1-carboxylic acid Alternatively to the procedures of Example 3.II.E., by using the method of Example 4.I.b., but substituting the aroyl ester (VII) by N-alkyl-2-pyrrolyl or N-alkyl-3-pyrrolyl methyl esters of Example 1.II.E., 5-(N-alkyl-2-pyrrolyl)-6-alkylthio-1,2-dihydro-3-H-pyrrolo[1,2-a]pyrrole-1-carboxylic acid or 5-(N-alkyl-3-pyrrolyl)-6-alkylthio-1,2-dihydro-3H-pyrrolo[1,2-a]pyrrole-1-carboxylic acid are prepared.

EXAMPLE 5

I. Synthesis of methyl-5-aroyl-6-alkylsulfinyl-1,2-dihydro-3H-pyrrolo[1,2-a]pyrrole-1-carboxylates This example illustrates a method, according to the invention, of preparing alkyl esters of 5-aroyl-6-alkylsulfinyl-1,2-dihydro-3H-pyrrolo[1,2-a]-pyrrole.

A solution of sodium periodate (5.58 g, 27 mmol) in water (90 ml) is added to a stirred suspension of compound (VII) (2.50 g, 6.3 mmol) in methanol (350 ml) at 0° C. The reaction temperature is left to rise to 20° C. and after 1.5 h the reaction is observed to be complete by TLC. The methanol is removed at reduced pressure, the aqueous residue is saturated with sodium chloride, and the product is extracted into ethyl acetate. The extract is washed with dilute sodium bicarbonate solution and with water, and then it is dried over sodium sulfate. The solvent is removed in vacuo.

II. Synthesis of specific compounds

A. Synthesis of methyl 5-benzoyl-6-alkylsulfinyl-1,2-dihydro-3H-pyrrolo[1,2-a]pyrrole-1-carboxylates a. Synthesis of methyl 5-benzoyl-6-methylsulfinyl-1,2-dihydro-3H-pyrrolo-[1,2-a]pyrrole-1-carboxylates The following method is used for the preparation of methyl 5-benzoyl-6-methylsulfinyl-1,2-dihydro-3H-pyrrolo-[1,2-a]pyrrole-1-carboxylates wherein the starting methyl ester is chosen from those compounds of Example 1.II.A.a.1–11.

A solution of sodium periodate (5.58 g, 27 mmol) in water (90 ml) was added to a stirred suspension of compound (VII) (2.50 g, 6.3 mmol) in methanol (350 ml) at 0° C. The reaction temperature was left to come to 20° C. and after 1.5 h the reaction was observed to be complete by TLC. The methanol was removed at reduced pressure, the aqueous residue was saturated with sodium chloride, and the product was extracted into ethyl acetate. The extract was washed with dilute sodium bicarbonate solution and with water, and dried over sodium sulfate. The solvent was removed in vacuo giving the appropriate crude product in quantitative yield.

1. Methyl 5-(4-bromobenzoyl)-6-methylsulfinyl-1,2-dihydro-3H-pyrrolo[1,2-a]pyrrole-1-carboxylate In this manner using as the starting ester the compound of Example 1.II.A.a.1. methyl 5-(4-bromobenzoyl)-6-methylsulfinyl-1,2-dihydro-3H-pyrrolo[1,2-a]pyrrole-1-carboxylate was prepared. Compound was crystallized from methanol.
M.P.: 170°–171° C.

2. Similarly, in the same manner, using as a starting compound methyl esters of Example 1.II.A.a.2–11 the following compounds are prepared:
Methyl 5-(4-methylbenzoyl)-6-methylsulfinyl-1,2-dihydro-3H-pyrrolo[1,2-a]pyrrole-1-carboxylate;
Methyl 5-(4-vinylbenzoyl)-6-methylsulfinyl-1,2-dihydro-3H-pyrrolo[1,2-a]pyrrole-1-carboxylate;
Methyl 5-(4-ethylbenzoyl)-6-methylsulfinyl-1,2-dihyro-3H-pyrrolo[1,2-a]pyrrole-1-carboxylate;
Methyl 5-(4-ethoxybenzoyl)-6-methylsulfinyl-1,2-dihydro-3H-pyrrolo[1,2-a]pyrrole-1-carboxylate;
Methyl 5-(4-i-propoxybenzoyl)-6-methylsulfinyl-1,2-dihydro-3H-pyrrolo[1,2-a]pyrrole-1-carboxylate;
Methyl 5-(4-methylthiobenzoyl)-6-methylsulfinyl-1,2-dihydro-3H-pyrrolo[1,2-a]pyrrole-1-carboxylate;
Methyl 5-(4-trifluoromethyl-benzoyl)-6-methylsulfinyl-1,2-dihydro-3H-pyrrolo[1,2-a]-pyrrole-1-carboxylate;
Methyl 5-(4-cyclohexylbenzoyl)-6-methylsulfinyl-1,2-dihydro-3H-pyrrolo[1,2-a]pyrrole-1-carboxylate;
Methyl 5-(4-n-propylbenzoyl)-6-methylsulfinyl-1,2-dihydro-3H-pyrrolo[1,2-a]pyrrole-1-carboxylate;
Methyl 5-(4-cyclopropylbenzoyl)-6-methylsulfinyl-1,2-dihydro-3H-pyrrolo[1,2-a]pyrrole-1-carboxylate.

b. Methyl 5-(5-benzoyl)-6-alkylsulfinyl-1,2-dihydro-3H-pyrrolo[1,2-a]pyrrole-1-carboxylates Similarly, but using as starting compound a compound of formula (VII) methyl 5-benzoyl-6-alkylsulfinyl-1,2-dihydro-3H-pyrrolo[1,2-a]pyrrole-1-carboxylates are prepared.

B. Synthesis of methyl 5-(2-thenoyl)-6-alkylsulfinyl-1,2-dihydro-3H-pyrrolo[1,2-a]pyrrole-1-carboxylates or methyl-5-(3-thenoyl)-6-alkylsulfinyl-3-thenoyl-1,2-dihydro-3H-pyrrolo[1,2-a]-pyrrole-1-carboxylates Similarly, but using as a starting ester compounds of Example 1.II.B., the following compounds are prepared:
methyl 5-(2-thenoyl)-6-alkylsulfinyl-1,2-dihydro-3H-pyrrolo[1,2-a]pyrrole-1-carboxylates
methyl 5-(3-thenoyl)-6-alkylsulfinyl-1,2-dihydro-3H-pyrrolo[1,2-a]pyrrole-1-carboxylates are prepared.

C. Synthesis of methyl 5-(2-furoyl)-6-alkylsulfinyl-1,2-dihydro-3H-pyrrolo[1,2-a]pyrrole-1-carboxylates or methyl 5-(3-furoyl)-6-alkylsulfinyl-1,2-dihydro-3H-pyrrolo[1,2-a]pyrrole-1-carboxylates Similarly but using as a starting ester compounds of Example 1.II.C., the following compounds are prepared:
methyl 5-(2-furoyl)-6-alkylsulfinyl-1,2-dihydro-3H-pyrrolo[1,2-a]pyrrole-1-carboxylate;
methyl 5-(3-furoyl)-6-alkylsulfinyl-1,2-dihydro-3H-pyrrolo[1,2-a]pyrrole-1-carboxylate.

D. Synthesis of methyl 5-(2-pyrrolyl)-6-alkylsulfinyl-1,2-dihydro-3H-pyrrolo[1,2-a]pyrrole-1-carboxylates or methyl 5-(3-pyrrolyl)-6-alkylsulfinyl-1,2-dihydro-3H-pyrrolo[1,2-a]pyrrole-1-carboxylates Similarly but using as a starting ester compounds of Example 1.II.D., the following compounds are prepared:
methyl 5-(2-pyrrolyl)-6-alkylsulfinyl-1,2-dihydro-3H-pyrrolo[1,2-a]pyrrole-1-carboxylates;
methyl 5-(3-pyrrolyl)-6-alkylsulfinyl-1,2-dihydro-3H-pyrrolo[1,2-a]pyrrole-1-carboxylates.

E. Synthesis of methyl 5-(N-alkyl-2-pyrrolyl)-6-alkylsulfinyl-1,2-dihydro-3H-pyrrolo[1,2-a]pyrrole-1-carboxylates or methyl 5-(N-alkyl-3-pyrrolyl)-6-alkylsulfinyl-1,2-dihydro-3H-pyrrolo[1,2-a]pyrrole-1-carboxylates Similarly but using as a starting ester compounds of Example 1.II.E., the following compounds are prepared:
methyl 5-(N-alkyl-2-pyrrolyl)-6-alkylsulfinyl-1,2-dihydro-3H-pyrrolo[1,2-a]pyrrole-1-carboxylates;
methyl 5-(N-alkyl-3-pyrrolyl)-6-alkylsulfinyl-1,2-dihydro-3H-pyrrolo[1,2-a]pyrrole-1-carboxylates.

EXAMPLE 6

I. Synthesis of 5-aroyl-6-alkylsulfinyl-1,2-dihydro-3H-pyrrolo[1,2-a]pyrrole-1-carboxylic acid This example illustrates a method, according to the invention, of preparing 5-aroyl-6-alkylsulfinyl-1,2-dihydro-3H-pyrrolo[1,2-a]pyrrole-1-carboxylic acid.

To a solution of the ester prepared according to Example 5.I.b. (10 mmol) in methanol (60 ml) is added a solution of sodium hydroxide (2 eq.) in water (60 ml) and the resulting solution is stirred at room temperature for 8–18 hours The methanol is removed in vacuo and the aqueous residue is extracted twice with 50 ml of ether. The aqueous alkaline phase is made acidic with 10% hydrochloric acid and the product is extracted into ethyl acetate. The extract is washed with water, dried over sodium sulfate and evaporated in vacuo.

II. Synthesis of specific compounds

A. Synthesis of 5-benzoyl-6-alkylsulfinyl-1,2-dihydro-3H-pyrrolo[1,2-a]pyrrole-1-carboxylic acids a. Synthesis of 5-benzoyl-6-methylsulfinyl-1,2-dihydro-3H-pyrrolo[1,2-a]pyrrole-1-carboxylic acids The method of Example 6.I. is used for the preparation of 5-benzoyl-6-methylsulfinyl-1,2-dihydro-3H-pyrrolo[1,2-a]pyrrole-1-carboxylic acids wherein starting methyl ester is chosen from those compounds of Example 5.II.A.a.1. and 5.II.A.a.2.

1. 5-(4-bromobenzoyl)-6-methylsulfinyl-1,2-dihydro-3H-pyrrolo[1,2-a]pyrrole-1-carboxylic acid 5-(4-bromobenzoyl)-6-methylsulfinyl-1,2-dihydro-3H-pyrrolo[1,2-a]pyrrole-1-carboxylic acid was prepared by the following procedure.

To a solution of 10 mmol of the methyl 5-(4-bromobenzoyl)-6-methylsulfinyl-1,2-dihydro-3H-pyrrolo[1,2-a]-pyrrole-1-carboxylate (XII) in methanol (60 ml) was added a solution of sodium hydroxide (2 eq.) in 60 ml of water. The resulting solution was stirred at room temperature for 13 hours. The methanol was removed in vacuo and the aqueous residue was extracted twice with 50 ml of ether. The aqueous alkaline phase was made acidic with 10% hydrochloric acid and the product was extracted into ethyl acetate. The extract was washed with water, dried over sodium sulfate and evaporated in vacuo. The product was crystallized from methyl alcohol. Yield: 64% M.P.: 226°–227° C.

2. Similarly, in the same manner, by using as a starting ester compound of Example 5.II.A.a.2. the following carboxylic acids are prepared:
5-(4-methylbenzoyl)-6-methylsulfinyl-1,2-dihydro-3H-pyrrolo[1,2-a]pyrrole-1-carboxylic acid.
5-(4-methylbenzoyl)-6-methylsulfinyl-1,2-dihydro-3H-pyrrolo[1,2-a]pyrrole-1-carboxylic acid;
5-(4-vinylbenzoyl)-6-methvlsulfinyl-1,2-dihydro-3H-pyrrolo[1,2-a]pyrrole-1-carboxylic acid;
5-(4-ethylbenzoyl)-6-methylsulfinyl-1,2-dihydro-3H-pyrrolo[1,2-a]pyrrole-1-carboxylic acid;
5-(4-ethoxybenzoyl)-6-methylsulfinyl-1,2-dihydro-3H-pyrrolo[1,2-a]pyrrole-1-carboxylic acid;
5-(4-i-propoxybenzoyl)-6-methylsulfinyl-1,2-dihydro-3H-pyrrolo[1,2-a]pyrrole-1-carboxylic acid;
5-(4-methylthiobenzoyl)-6-methylsulfinyl-1,2-dihydro-3H-pyrrolo[1,2-a]pyrrole-1-carboxylic acid;
5-(4-trifluoromethylbenzoyl)-6-methylsulfinyl-1,2-dihydro-3H-pyrrolo[1,2-a]-pyrrole-1-carboxylic acid;
5-(4-cyclohexylbenzoyl)-6-methylsulfinyl-1,2-dihydro-3H-pyrrolo[1,2-a]pyrrole-1-carboxylic acid;
5-(4-n-propylbenzoyl)-6-methylsulfinyl-pyrrolo[1,2-a]pyrrole-1-carboxylic acid;
5-(4-cyclopropylbenzoyl)-6-methylsulfinyl-1,2-dihydro-3H-pyrrolo[1,2-a]pyrrole-1-carboxylic acid.

b. 5-benzoyl-6-alkylsulfinyl-1,2-dihydro-3H-pyrrolo[1,2-a]pyrrole-1-carboxylic acids Similarly, but using as starting compound an alkyl ester prepared by procedure of Example 5.II.A.b., 5-benzoyl-6-alkylsulfinyl-1,2-dihydro-3H-pyrrolo [1,2-a]pyrrole-1-carboxylic acids are prepared.

B. Synthesis of 5-(2-thenoyl)-6-alkylsulfinyl-1,2-dihydro-3H-pyrrolo[1,2-a]pyrrole-1-carboxylic acid or 5-(3-thenoyl)-6-alkylsulfinyl-3-thenoyl-1,2-dihydro-3H-pyrrolo[1,2-a]-pyrrole-1-carboxylic acid Similarly, by using as a starting ester compounds of Example 5.II.B. the following ccmpounds are prepared:
5-(2-thenoyl)-6-alkylsulfinyl-1,2-dihydro-3H-pyrrolo-[1,2-a]pyrrole-1-carboxylic acid;
5-(3-thenoyl)-6-alkylsulfinyl-1,2-dihydro-3H-pyrrolo[1,2-a]pyrrole-1-carboxylic acid.

C. Synthesis of 5-(2-furoyl)-6-alkylsulfinyl-1,2-dihydro-3H-pyrrolo[1,2-a]pyrrole-1-carboxylic acid; 5-(3-furoyl)-6-alkylsulfinyl-1,2-dihydro-3H-pyrrolo[1,2-a]pyrrole-1-carboxylic acid Similarly, by using as a starting ester compounds of Example 5.II.C. the following compounds are prepared:
5-(2-furoyl)-6-alkylsulfinyl-1,2-dihydro-3H-pyrrolo[1,2-a]pyrrole-1-carboxylic acid;
5-(3-furoyl)-6-alkylsulfinyl-1,2-dihydro-3H-pyrrolo-[1,2-a]pyrrole-1-carboxylic acid.

D. Synthesis of 5-(2-pyrrolyl)-6-alkylsulfinyl-1,2-dihydro-3H-pyrrolo[1,2-a]pyrrole-1-carboxylic acid or 5-(3-pyrrolyl)-6-alkylsulfinyl-1,2-dihydro-3H-pyrrolo[1,2-a]-pyrrole-1-carboxylic acid Similarly, by using as a starting ester compounds of Example 5.II.D. the following compounds are prepared:
5-(2-pyrrolyl)-6-alkylsulfinyl-1,2-dihydro-3H-pyrrolo[1,2-a]pyrrole-1-carboxylic acid;
5-(3-pyrrolyl)-6-alkylsulfinyl-1,2-dihydro-3-H-pyrrolo[1,2-a]pyrrole-1-carboxylic acid.

E. Synthesis of 5-(N-alkyl-2-pyrrolyl)-6-alkylsulfinyl-1,2-dihydro-3H-pyrrolo[1,2-a]pyrrole-1-carboxylic acid or 5-(N-alkyl-3-pyrrolyl)-6-alkylsulfinyl-1,2-dihydro-3H-pyrrolo[1,2-a]pyrrole-1-carboxylic acid Similarly, by using as a starting ester compounds of Example 5.II.E. the following compounds are prepared:
5-(N-alkyl-2-pyrrolyl)-6-alkylsulfinyl-1,2-dihydro-3H-pyrrolo[1,2-a]pyrrole-1-carboxylic acid;
5-(N-alkyl-3-pyrrolyl)-6-alkylsulfinyl-1,2-dihydro-3H-pyrrolo[1,2-a]pyrrole-1-carboxylic acid.

EXAMPLE 7

I. Synthesis of methyl 5-aroyl-6-alkylsulfonyl-1,2-dihydro-3H-pyrrolo[1,2-a]pyrrole-1-carboxylates This example illustrates a method, according to the invention, of preparing methyl of 5-aroyl-6-alkylsulfonyl-1,2-dihydro-3H-pyrrolo[1,2-a]pyrrole-1-carboxylic acid.

Solid m-chloroperbenzoic acid (3.30 g, 19 mmol) is added in portions to a stirred solution of the compound (VII) (2.50 g, 6.3 mmol) in 150 ml of anhydrous dichloromethane (150 ml) at 0° C. After 1 h at 0° C. the solution is washed successively with dilute sodium bicarbonate solution and water. The organic phase is dried over sodium sulfate and evaporated in vacuo. The crude product was obtained in 84% yield.

II. Synthesis of specific compounds

A. Synthesis of methyl 5-aroyl-6-alkylsulfonyl-1,2-dihydro-3H-pyrrolo[1,2-a]pyrrole-1-carboxylates a. Synthesis of methyl 5-benzoyl-6-methylsulfonyl-1,2-dihydro-3H-pyrrolo[1,2-a]pyrrole-1-carboxylates The method of Example 7.I. is used for the preparation of methyl 5-benzoyl-6-methylsulfonyl-1,2-dihydro-3H-pyrrolo[1,2-a]pyrrole-1-carboxylates wherein the starting methyl ester is chosen from those compounds of Example 1.II.A.a.1-11.

Solid m-chloroperbenzoic acid (3.30 g, 19 mmol) was added in portions to a stirred solution of the compound (VII) (2.50 g, 6.3 mmol) in 150 ml of anhydrous dichloromethane (150 ml) at 0° C. After 1 h at 0° C. the solution was washed successively with dilute sodium bicarbonate solution and water. The organic phase was dried over sodium sufate and evaporated in vacuo. The crude product was obtained in 84% yield.

1. Methyl 5-(4-bromobenzoyl)-6-methylsulfonyl-1,2-dihydro-3H-pyrrolo[1,2-a]pyrrole-1-carboxylate In this manner, using the compound of Example 1.II.A.a.1. as a starting methyl ester methyl 5-(4-bromobenzoyl)-6-methylsulfonyl-1,2-dihydro-3H-pyrrolo-[1,2-a]pyrrole-1-carboxylate was prepared.

M.P.: 153°–154° C. (dichloromethane-methanol)

2. Similarly, in the same manner, by using as a starting compound methyl esters of Example 1.II.A.a.2-11, the following compounds are prepared:

Methyl 5-(4-methylbenzoyl)-6-methylsulfonyl-1,2-dihydro-3H-pyrrolo[1,2-a]pyrrole-1-carboxylate;
Methyl 5-(4-vinylbenzoyl)-6-methylsulfonyl-1,2-dihydro-3H-pyrrolo[1,2-a]pyrrole-1-carboxylate;
Methyl 5-(4-ethylbenzoyl)-6-methylsulfonyl-1,2-dihydro-3H-pyrrolo[1,2-a]pyrrole-1-carboxylate;
Methyl 5-(4-ethoxybenzoyl)-6-methylsulfonyl-1,2-dihydro-3H-pyrrolo[1,2-a]pyrrole-1-carboxylate;
Methyl 5-(4-i-propoxybenzoyl)-6-methylsulfonyl-1,2-dihydro-3H-pyrrolo[1,2-a]pyrrole-1-carboxylate;
Methyl 5-(4-methylthiobenzoyl)-6-methylsulfonyl-1,2-dihydro-3H-pyrrolo[1,2-a]pyrrole-1-carboxylate;
Methyl 5-(4-trifluoromethylbenzoyl)-6-methylsulfonyl-1,2-dihydro-3H-pyrrolo[1,2-a]-pyrrole-1-carboxylate;
Methyl 5-(4-cyclohexylbenzoyl)-6-methylsulfonyl-1,2-dihydro-3H-pyrrolo[1,2-a]pyrrole-1-carboxylate;
Methyl 5-(4-n-propylbenzoyl)-6-methylsulfonyl-1,2-dihydro-3H-pyrrolo[1,2-a]pyrrole-1-carboxylate;
Methyl 5-(4-cyclopropylbenzoyl)-6-methylsulfonyl-1,2-dihydro-3H-pyrrolo[1,2-a]pyrrole-1-carboxylate.

b. Methyl 5-benzoyl-6-alkylsulfonyl-1,2-dihydro-3H-pyrrolo[1,2-a]pyrrole-1-carboxylates Similarly but using as a starting compound an alkylsulfonyl compound of formula (VII) methyl 5-benzoyl-6-alkylsulfonyl-1,2-dihydro-3H-pyrrolo[1,2-a]pyrrole-1-carboxylates are prepared.

B. Synthesis of methyl 5-(2-thenoyl)-6-alkylsulfonyl-1,2-dihydro-3H-pyrrolo[1,2-a]pyrrole-1-carboxylates or methyl-5-(3-thenoyl)-6-alkylsulfonyl-3-thenoyl-1,2-dihydro-3H-pyrrolo[1,2-a]pyrrole-1-carboxylates Similarly, but using as a starting ester compounds of Example 1.II.B., the following compounds are prepared:
methyl 5-(2-thenoyl)-6-alkylsulfonyl-1,2-dihydro-3H-pyrrolo[1,2-a]pyrrole-1-carboxylate;
methyl 5-(3-thenoyl)-6-alkylsulfonyl-1,2-dihydro-3H-pyrrolo[1,2-a]pyrrole-1-carboxylates.

C. Synthesis of methyl 5-(2-furoyl)-6-alkylsulfonyl-1,2-dihydro-3H-pyrrolo[1,2-a]pyrrole-1-carboxylates or methyl 5-(3-furoyl)-6-alkylsulfonyl-1,2-dihydro-3H-pyrrolo[1,2-a]pyrrole-1-carboxylates Similarly but using as a starting ester ccmpounds of Example 1.II.C., the following compounds are prepared:
methyl 5-(2-furoyl)-6-alkylsulfonyl-1,2-dihydro-3H-pyrrolo[1,2-a]pyrrole-1-carboxylate;
methyl 5-(3-furoyl)-6-alkylsulfonyl-1,2-dihydro-3H-pyrrolo[1,2-a]pyrrole-1-carboxylate.

D. Synthesis of methyl 5-(2-pyrrolyl)-6-alkylsulfonyl-1,2-dihydro-3H-pyrrolo[1,2-a]pyrrole-1-carboxylates or methyl 5-(3-pyrrolyl)-6-alkylsulfonyl-1,2-dihydro-3H-pyrrolo[1,2-a]pyrrole-1-carboxylates Similarly but using as a starting ester compounds of Example 1.II.D., the following ccmpounds are prepared:
methyl 5-(2-pyrrolyl)-6-alkylsulfonyl-1,2-dihydro-3H-pyrrolo[1,2-a]pyrrole-1-carboxylate;
methyl 5-(3-pyrrolyl)-6-alkylsulfonyl-1,2-dihydro-3H-pyrrolo[1,2-a]pyrrole-1-carboxylate.

E. Synthesis of methyl 5-(N-alkyl-2-pyrrolyl)-6-alkylsulfonyl-1,2-dihydro-3H-pyrrolo[1,2-a]pyrrole-1-carboxylates or methyl 5-(N-alkyl-3-pyrrolyl)-6-alkylsulfonyl-1,2-dihydro-3H-pyrrolo[1,2-a]pyrrole-1-carboxylates Similarly but using as a starting ester compounds of Example 1.II.E., the following compounds are prepared:
methyl 5-(N-alkyl-2-pyrrolyl)-6-alkylsulfonyl-1,2-dihydro-3H-pyrrolo[1,2-a]pyrrole-1-carboxylate;
methyl 5-(N-alkyl-3-pyrrolyl)-6-alkylsulfonyl-1,2-dihydro-3H-pyrrolo[1,2-a]pyrrole-1-carboxylate.

EXAMPLE 8

I. Synthesis of 5-aroyl-6-alkylsulfonyl-1,2-dihydro-3H-pyrrolo[1,2-a]pyrrole-1-carboxylic acid This example illustrates a method, according to the invention, of preparing 5-aroyl-6-alkylsulfonyl-1,2-dihydro-3H-pyrrolo[1,2-a]pyrrole-1-carboxylic acid.

To a solution of the ester prepared according to Example 7.I. (10 mmol) in methanol (60 ml) was added a solution of sodium hydroxide (2 eq.) in water (60 ml) and the resulting solution was stirred at room temperature for 0.5–2 hours. The methanol was removed in vacuo and the aqueous residue was extracted twice with 50 ml ether. The aqueous alkaline phase was made acidic with 10% hydrochloric acid and the product was extracted into ethyl acetate. The extract was washed with water, dried over sodium sulfate and evaporated in vacuo.

II. Synthesis of specific compounds

A. Synthesis of 5-aroyl-6-alkylsulfonyl-1,2-dihydro-3H-pyrrolo[1,2-a]pyrrole-1-carboxylic acid a. Synthesis of 5-benzoyl-6-methylsulfonyl-1,2-dihydro-3H-pyrrolo[1,2-a]pyrrole-1-carboxylic acids The method of Example 8.I. is used for the preparation of 5-benzoyl-6-methylsulfonyl-1,2-dihydro-3H-pyrrolo[1,2-a]pyrrole-1-carboxylic acids wherein starting methyl ester is chosen from those compounds of Example 7.II.A.a.1. and 7.II.A.a.2.

1. 5-(4-bromobenzoyl)-6-methylsulfonyl-1,2-dihydro-3H-pyrrolo[1,2-a]pyrrole-1-carboxylic acid 5-(4-bromobenzoyl)-6-methylsulfonyl-1,2-dihydro-3H-pyrrolo[1,2-a]pyrrole-1-carboxylic acid is prepared by the following procedure.

To a solution of the methyl 5-(4-bromobenzoyl)-6-methylsulfonyl-1,2-dihydro-3H-pyrrolo[1,2-a]pyrrole-1-carboxylate (10 mmol) in methanol (60 ml) was added a solution of sodium hydroxide (2 equivalents) in water (60 ml) and the resulting solution was stirred at room temperature for ¾ hours. The methanol was removed in vacuo and the aqueous residue was extracted twice with 50 ml of ether. The aqueous alkaline phase was made acidic with 10% hydrochloric acid and the product was extracted into ethyl acetate. The extract was washed with water, dried over sodium sulfate and evaporated in vacuo. The product was crystallized from methanol. Yield: 76%.

M.P.: 226°–227° C.

2. Similarly, in the same manner, by using as a starting ester ccmpound methyl esters of Example 7.II.A.a.2. the following carboxylic acids were prepared:
5-(4-methylbenzoyl)-6-methylsulfonyl-1,2-dihydro-3H-pyrrolo[1,2-a]pyrrole-1-carboxylic acid;
5-(4-methylbenzoyl)-6-methylsulfonyl-1,2-dihydro-3H-pyrrolo[1,2-a]pyrrole-1-carboxylic acid;
5-(4-vinylbenzoyl)-6-methylsulfonyl-1,2-dihydro-3H-pyrrolo[1,2-a]pyrrole-1-carboxylic acid;
5-(4-ethylbenzoyl)-6-methylsulfonyl-1,2-dihydro-3H-pyrrolo[1,2-a]pyrrole-1-carboxylic acid;
5-(4-ethoxybenzoyl)-6-methylsulfonyl-1,2-dihydro-3H-pyrrolo[1,2-a]pyrrole-1-carboxylic acid;
5-(4-i-propoxybenzoyl)-6-methylsulfonyl-1,2-dihydro-3H-pyrrolo[1,2-a]pyrrole-1-carboxylic acid;
5-(4-methylthiobenzoyl)-6-methylsulfonyl-1,2-dihydro-3H-pyrrolo[1,2-a]pyrrole-1-carboxylic acid;
5-(4-trifluoromethylbenzoyl)-6-methylsulfonyl-1,2-dihydro-3H-pyrrolo[1,2-a]pyrrole-1-carboxylic acid;
5-(4-cyclohexylbenzoyl)-6-methylsulfonyl-1,2-dihydro-3H-pyrrolo[1,2-a]pyrrole-1-carboxylic acid;
5-(4-n-propylbenzoyl)-6-methylsulfonyl-1,2-dihydro-3H-pyrrolo[1,2-a]pyrrole-1-carboxylic acid;
5-(4-cyclopropylbenzoyl)-6-methylsulfonyl-1,2-dihydro-3H-pyrrolo[1,2-a]pyrrole-1-carboxylic acid.

b. 5-benzoyl-6-alkylsulfonyl-1,2-dihydro-3H-pyrrolo[1,2-a]pyrrole-1-carboxylic acids Similarly, but using as starting compound an alkyl ester prepared by procedure of Example 7.II.A.b., 5-benzoyl-6-alkylsulfonyl-1,2-dihydro-3H-pyrrolo[1,2-a]pyrrole-1-carboxylic acids are prepared.

B. Synthesis of 5-(2-thenoyl)-6-alkylsulfonyl-1,2-dihydro-3H-pyrrolo[1,2-a]pyrrole-1-carboxylic acid or 5-(3-thenoyl)-6-alkylsulfonyl-3-thenoyl-1,2-dihydro-3H-pyrrolo[1,2-a]pyrrole-1-carboxylic acid Similarly, by using as a starting ester compounds of Example 7.II.B. the following compounds are prepared:
5-(2-thenoyl)-6-alkylsulfonyl-1,2-dihydro-3H-pyrrolo[1,2-a]pyrrole-1-carboxylic acid;
5-(3-thenoyl)-6-alkylsulfonyl-1,2-dihydro-3H-pyrrolo[1,2-a]pyrrole-1-carboxylic acid.

C. Synthesis of 5-(2-furoyl)-6-alkylsulfonyl-1,2-dihydro-3H-pyrrolo[1,2-a]pyrrole-1-carboxylic acid or 5-(3-furoyl)-6-alkylsulfonyl-1,2-dihydro-3H-pyrrolo[1,2-a]pyrrole-1-carboxylic acid Similarly, by using as a starting ester compounds of Example 7.II.C. the following compounds are prepared:
5-(2-furoyl)-6-alkylsulfonyl-1,2-dihydro-3H-pyrrolo[1,2-a]pyrrole-1-carboxylic acid;
5-(3-furoyl)-6-alkylsulfonyl-1,2-dihydro-3H-pyrrolo[1,2-a]pyrrole-1-carboxylic acid.

D. Synthesis of 5-(2-pyrrolyl)-6-alkylsulfonyl-1,2-dihydro-3H-pyrrolo[1,2-a]pyrrole-1-carboxylic acid or 5-(3-pyrrolyl)-6-alkylsulfonyl-1,2-dihydro-3H-pyrrolo[1,2-a]pyrrole-1-carboxylic acid Similarly, by using as a starting ester compounds of Example 7.II.D. the following compounds are prepared:
5-(2-pyrrolyl)-6-alkylsulfonyl-1,2-dihydro-3H-pyrrolo[1,2-a]pyrrole-1-carboxylic acid;
5-(3-pyrrolyl)-6-alkylsulfonyl-1,2-dihydro-3H-pyrrolo[1,2-a]pyrrole-1-carboxylic acid.

E. Synthesis of 5-(N-alkyl-2-pyrrolyl)-6-alkylsulfonyl-1,2-dihydro-3H-pyrrolo[1,2-a]pyrrole-1-carboxylic acid or 5-(N-alkyl-3-pyrrolyl)-6-alkylsulfonyl-1,2-dihydro-3H-pyrrolo[1,2-a]pyrrole-1-carboxylic acid Similarly, by using as a starting ester compounds of Example 7.II.E. the following ccmpounds are prepared:
5-(N-alkyl-2-pyrrolyl)-6-alkylsulfonyl-1,2-dihydro-3H-pyrrolo[1,2-a]pyrrole-1-carboxylic acid;
5-(N-alkyl-3-pyrrolyl)-6-alkylsulfonyl-1,2-dihydro-3H-pyrrolo[1,2-a]pyrrole-1-carboxylic acid.

EXAMPLE 9

This example illustrates conversion of free carboxylic acids of Examples 3, 4, 6, and 8 to various esters.

A solution of 200 mg of 5-benzoyl-6-methylthio-1,2-dihydro-3H-pyrrolo[1,2-a]pyrrole-1-carboxylic acid in 5 ml of dichloromethane is treated with an excess of ethereal diazomethane, and the reaction mixture is maintained at room temperature for 30 minutes. The solvents and excess reagent are eliminated under reduced pressure and the residue crystallized from ethyl acetate-methanol, to yield methyl 5-benzoyl-6-methylthio-1,2-dihydro-3H-pyrrolo[1,2-a]pyrrole-1-carboxylate.

Likewise but using diazoethane, diazopropane and diazobutane in place of diazoethane there are respectively obtained ethyl 5-benzoyl-6-methylthio-1,2-dihydro-3H-pyrrolo-[1,2-a]pyrrole-1-carboxylate,
propyl 5-benzoyl-6-methylthio-1,2-dihydro-3H-pyrrolo[1,2-a]pyrrole-1-carboxylate and
butyl 5-benzoyl-6-methylthio-1,2-dihydro-3H-pyrrolo[1,2-a]pyrrole-1-carboxylate.

In a similar manner, the remaining free acids obtained in Examples 3, 4, 6 and 8 are converted into the corresponding methyl, ethyl, propyl and butyl esters.

EXAMPLE 10

This example illustrates conversion of free carboxylic acids of Examples 3, 4, 6, and 8 to various other esters.

A solution of 300 mg of 5-benzoyl-6-methylthio-1,2-dihydro-3H-pyrrolo[1,2-a]pyrrole-1-carboxylic acid in 5 ml of isoamyl alcohol is saturated with hydrogen chloride. After 24 hours, the excess alcohol is distilled off in vacuo and the residue purified by chromatography on alumina, to yield isoamyl 5-benzoyl-6-methylthio-1,2-dihydro-3H-pyrrolo[1,2-a]pyrrole-1-carboxylate.

Likewise other esters, e.g., pentyl, hexyl, octyl, nonyl, dodecyl, and the like are obtained by substituting other alcohols, e.g., pentyl, hexyl, octyl, nonyl, dodecyl alcohol, and the like, for isoamyl alcohol.
pentyl 5-benzoyl-6-methylthio-1,2-dihydro-3H-pyrrolo[1,2-a]pyrrole-1-carboxylate,
hexyl 5-benzoyl-6-methylthio-1,2-dihydro-3H-pyrrolo[1,2-a]pyrrole-1-carboxylate,
octyl 5-benzoyl-6-methylthio-1,2-dihydro-3H-pyrrolo[1,2-a]pyrrole-1-carboxylate,
nonyl 5-benzoyl-6-methylthio-1,2-dihydro-3H-pyrrolo[1,2-a]pyrrole-1-carboxylate,
dodecyl 5-benzoyl-6-methylthio-1,2-dihydro-3H-pyrrolo[1,2-a]pyrrole-1-carboxylate, By the same method the free acid compounds obtained in Examples 3, 4, 6 and 8 are esterified with the appropriate alcohol thus obtaining the corresponding esters.

EXAMPLE 11

This Example illustrates conversion of free carboxylic acid of Examples 3, 4, 6 and 8 to various salts.

To a solution of 300 mg of 5-benzoyl-6-methylthio-1,2-dihydro-3H-pyrrolo[1,2-a]pyrrole-1-carboxylic acid in 5 ml of methanol is added 1 molar equivalent of sodium hydroxide, in the form of a 0.1N solution. The solvent is evaporated in vacuo and the residue is taken up in 2 ml of methanol, followed by precipitation with ether, to yield crude sodium 5-benzoyl-6-methylthio-1,2-dihydro-3H-pyrrolo[1,2-a]-pyrrole-1-carboxylate.

Likewise other salts, e.g., ammonium of 5-benzoyl-6-methylthio-1,2-dihydro-3H-pyrrolo[1,2-a]pyrrole-1-carboxylic acid are prepared by substituting ammonium hydroxide and potassium hydroxide for sodium hydroxide.

In a similar manner, the remaining free acids obtained in Examples 3, 4, 6 and 8 can be converted into the corresonding sodium, potassium and ammonium salts.

EXAMPLE 12

This Example illustrates conversion of free carboxylic acid of Examples 3, 4, 6 and 8 to various other salts.

To a solution of 175 mg of 5-benzoyl-6-methylthio-1,2-dihydro-3H-pyrrolo[1,2-a]pyrrole-1-carboxylic acid in 5 ml of methanol is added 1 molar equivalent of potassium hydroxide, in the form of a 0.1N solution, thus yielding a solution containing potassium 5-benzoyl-6-methylthio-1,2-dihydro-3H-pyrrolo[1,2-a]pyrrole-1-carboxylate.

A solution of 40 mg of calcium carbonate dissolved in the minimum amount of 1N hydrochloric acid necessary to effect solution of the calcium carbonate, is buffered with 100 mg of solid ammonium chloride, followed by the further addition of 5 ml of water. The thus obtained buffered calcium solution is then added to the solution of potassium 5-benzoyl-6-methylthio-1,2-dihydro-3H-pyrrolo[1,2-a]pyrrole-1-carboxylate and the precipitate which forms is collected by filtration, washed with water and air dried to yield calcium 5-benzoyl-6-methylthio-1,2-dihydro-3H-pyrrolo[1,2-a]-pyrrole-1-carboxylate.

Likewise, magnesium 5-benzoyl-6-methylthio-1,2-dihydro-3H-pyrrolo[1,2-a]pyrrole-1-carboxylate is prepared by substituting magnesium carbonate for calcium carbonate.

Similarly, the remaining free carboxylic acids of Examples 3, 4 and 8 can be converted to corresponding potassium calcium and magnesium salts.

EXAMPLE 13

| Ingredients | Quantity per tablet, mgs. |
|---|---|
| 5-benzoyl-6-methylthio-1,2-dihydro-3H—pyrrolo[1,2-a]-pyrrole-1-carboxylic acid | 25 |
| cornstarch | 20 |
| lactose, spray-dried | 153 |
| magnesium stearate | 2 |

The above ingredients are thoroughly mixed and pressed into single scored tablets.

Other carboxylic acids or their esters or salts of Examples 1–12 can be substituted for the compound of the above composition.

EXAMPLE 14

| Ingredients | Quantity per capsule, mgs. |
|---|---|
| 5-benzoyl-6-methylthio-1,2-dihydro-3H—pyrrolo[1,2-a]-pyrrole-1-carboxylic acid | 100 |
| lactose | 148 |
| magnesium stearate | 2 |

The above ingredients are mixed and introduced into a hard-shell gelatin capsule.

Other free acids, their salts or esters of Examples 1–12 can be is substituted for the compound of the above composition.

EXAMPLE 15

| Ingredients | Quantity per capsule, mgs. |
|---|---|
| 5-benzoyl-6-methylthio-1,2-dihydro-3H—pyrrolo[1,2-a]-pyrrole-1-carboxylic acid | 200 |
| cornstarch | 50 |
| lactose | 145 |
| magnesium stearate | 5 |

The above ingredients are mixed intimately and pressed into single scored tablets.

EXAMPLE 16

| Ingredients | Quantity per capsule, mgs. |
| --- | --- |
| 5-(4-chlorobenzoyl)-6-methyl-thio-1,2-dihydro-3H—pyrrolo[1,2-a]pyrrole-1-carboxylic acid | 108 |
| lactose | 15 |
| cornstarch | 25 |
| magnesium stearate | 2 |

The above ingredients are mixed and introduced into a hard-shell gelatin capsule.

EXAMPLE 17

| Ingredients | Quantity per capsule, mgs. |
| --- | --- |
| 5-benzoyl-6-methylthio-1,2-dihydro-3H—pyrrolo[1,2-a]pyrrole-1-carboxylate acid | 115 |
| lactose | 93 |
| cornstarch | 40 |
| magnesium stearate | 2 |

The above ingredients are mixed and introduced into a hard-shell gelatin capsule.

EXAMPLE 18

| Ingredients | Quantity per capsule, mgs. |
| --- | --- |
| 5-benzoyl-6-methylthio-1,2-dihydro-3H—pyrrolo[1,2-a]pyrrole-1-carboxylic acid | 100 |
| sucrose | 100 |

The above ingredients are thoroughly mixed and processed into single scored tablets.

EXAMPLE 19

| Ingredients | Quantity per capsule, mgs. |
| --- | --- |
| 5-benzoyl-6-methylthio-1,2-dihydro-3H—pyrrolo[1,2-a]pyrrole-1-carboxylic acid | 254 |
| cornstarch | 50 |
| lactose | 190 |
| magnesium stearate | 6 |

The above ingredients are mixed intimately and pressed into single scored tablets.

EXAMPLE 20

| Ingredients | Quantity per capsule, mgs. |
| --- | --- |
| 5-benzoyl-6-methylthio-1,2-dihydro-3H—pyrrolo[1,2-a]pyrrole-1-carboxylic acid | 100 |
| lactose | 148 |
| dextrose | 2 |

The above ingredients are mixed and introduced into a hard-shell gelatin capsule.

EXMAPLE 21

| Ingredients | Quantity per capsule, mgs. |
| --- | --- |
| 5-(4-(chlorobenzoyl)-6-methylthio-1,2-dihydro-3H—pyrrolo[1,2-a]pyrrole-1-carboxylic acid | 150 |
| lactose | 92 |

The above ingredients are mixed and introduced into a hard-shell gelatin capsule.

EXAMPLE 22

An injectable preparation buffered to a pH of 7 is prepared having the following composition:

| | |
| --- | --- |
| 5-benzoyl-6-methylthio-1,2-dihydro-3H—pyrrolo[1,2-a]pyrrole-1-carboxylic acid | 0.2 g |
| $K_2HPO_4$ buffer (0.4 M solution) | 2 ml. |
| KOH (1N) q.s. to | pH 7 |
| water (distilled sterile) q.s. to | 20 ml. |

Other carboxylic acids of this invention may be substituted for the compound of the above composition.

EXAMPLE 23

A suppositiory totaling 2.5 grams is prepared having the following composition:

| | |
| --- | --- |
| 5-benzoyl-6-methylthio-1,2-dihydro-3H—pyrrolo[1,2-a]pyrrole-1-carboxylic acid | 25 mg. |
| Witepsol H-15 (triglycerides of saturated vegetable fatty acids; a product of Riches-Nelson, Inc., New York, N.Y.) | balance |

Other carboxylic acids of this invention may be substituted for the compound of the above composition.

EXAMPLE 24

An oral suspension is prepared having the following composition:

| | |
| --- | --- |
| 5-benzoyl-6-methylthio-1,2-dihydro-3H—pyrrolo[1,2-a]pyrrole-1-carboxylic acid | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water q.s. to | 100 ml |

Other carboxylic acids of this invention may be substituted for the compound of the above composition.

EXAMPLE 25

Screening test for anti-inflammatory activity

The oral anti-inflammatory activity is determined utilizing carrageenin induced paw inflammation in the rat in accordance with the method of Winter et al, *Pro. Soc. Exp. Biol. Med.* 111:544–547, (1962).

Materials and Methods

Female rats weighing 80–90 grams are used. The tested compounds are given at hour 0 orally by gavage in 1 ml aqueous vehicle. At hour 1, 0.05 ml of a 1% solution (in 0.9% NaCl) of carrageenin is injected the right hind paw. This injection causes an inflammation of the paw. The rats are sacrificed at hour 4, at which time both hind paws are removed and weighed separately.

End Point

The % increase in paw size is calculated as follows:

$$\frac{\text{Wt. of Right Paw} - \text{Wt. of Left Paw}}{\text{Wt. of Left Paw}} \times 100$$

The smaller the % increase in paw size, the lesser the degree of inflammation and the greater the anti-inflammatory activity.

Compounds of this invention show relatively high anti-inflammatory activity in this test.

EXAMPLE 26

Screening Test for analgetic activity

The oral analgetic activity potential is determined utilizing the mouse analgetic (anti-writhing) assay in accordance with the method of Hendershot and Forsaith (J. Pharmacol. Exp. Ther., 125:237–240, 1959)

Materials and Methods

The tested compounds are administered orally by gavage in an aqueous vehicle at time 0 to 18–20 gram male Swiss-Webster mice. Twenty minutes later 0.25 ml of a 0.02% solution of phenylquinone is injected intraperitoneally. This solution induces writhing.

End point

The total number of mice that writhe and the average number of writhes per mouse indicates the activity of the compound tested; the fewer writhes per mouse indicates a greater activity.

In this assay compounds of this invention show potent analgetic activity.

What is claimed is:

1. A compound selected from the group of those represented by the formula:

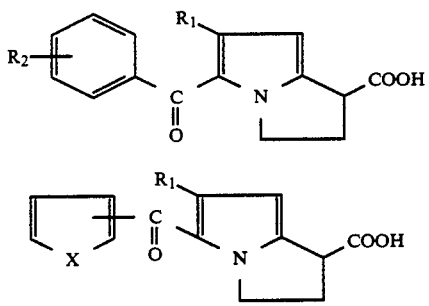

and the pharmaceutically acceptable, non-toxic esters and salts thereof, wherein
$R_1$ is lower alkylthio, lower alkylsulfinyl, or lower alkylsulfonyl;
$R_2$ is hydrogen, hydroxy, lower alkyl, vinyl, cyclohexyl, cyclopropyl, lower alkoxy, fluoro, chloro, bromo, trifluoromethyl, trifluoromethoxy, nitro, amino, lower alkylcarbonylamino, lower alkylthio, lower alkylsulfonyl or lower alkylsulfinyl;
X is oxygen, sulfur or N—$R_3$ where $R_3$ is hydrogen or lower alkyl.

2. A compound of claim 1, selected from the group of compounds represented by formula (1) and the pharmaceutically acceptable, non-toxic esters and salts thereof.

3. A compound of claim 2, wherein $R_1$ is methylthio.

4. A compound of claim 3, wherein $R_2$ is hydrogen, namely 5-benzoyl-6-methylthio-1,2-dihydro-3H-pyrrolo-[1,2-a]pyrrole-1-carboxylic acid and the pharmaceutically acceptable, non-toxic esters and salts thereof.

5. A compound of claim 3, wherein $R_2$ is fluoro, namely 5-(4-fluorobenzoyl)-6-methylthio-1,2-dihydro-3H-pyrrolo[1,2-a]pyrrole-1-carboxylic acid and the pharmaceutically acceptable, non-toxic esters and salts thereof.

6. A compound of claim 3, wherein $R_2$ is chloro, namely 5-(4-chlorobenzoyl)-6-methylthio-1,2-dihydro-3H-pyrrolo[1,2-a]pyrrole-1-carboxylic acid and the pharmaceutically acceptable, non-toxic esters and salts thereof.

7. A compound of claim 3, wherein $R_2$ is methoxy, namely 5-(4-methoxybenzoyl)-6-methylthio-1,2-dihydro-3H-pyrrolo[1,2-a]pyrrole-1-carboxylic acid and the pharmaceutically acceptable, non-toxic esters and salts thereof.

8. A compound of claim 3, wherein $R_2$ is bromo, namely 5-(4-bromobenzoyl)-6-methylthio-1,2-dihydro-3H-pyrrolo[1,2-a]pyrrole-1-carboxylic acid and the pharmaceutically acceptable, non-toxic esters and salts thereof.

9. The methyl ester of the compound of claim 8, namely methyl 5-(4-bromobenzoyl)-6-methylthio-1,2-dihydro-3H-pyrrolo[1,2-a]pyrrole-1-carboxylate.

10. A compound of claim 3, wherein $R_2$ is methyl, namely 5-(4-methylbenzoyl)-6-methylthio-1,2-dihydro-3H-pyrrolo[1,2-a]pyrrole-1-carboxylic acid and the pharmaceutically acceptable, non-toxic esters and salts thereof.

11. The methyl ester of the compound of claim 10, namely methyl 5-(4-methylbenzoyl)-6-methylthio-1,2-dihydro-3H-pyrrolo[1,2-a]pyrrole-1-carboxylate.

12. A compound of claim 3, wherein $R_2$ is vinyl, namely 5-(4-vinylbenzoyl)-6-methylthio-1,2-dihydro-3H-pyrrolo[1,2-a]pyrrole-1-carboxylic acid and the pharmaceutically acceptable, non-toxic esters and salts thereof.

13. The methyl ester of the compound of claim 12, namely methyl 5-(4-vinylbenzoyl)-6-methylthio-1,2-dihydro-3H-pyrrolo[1,2-a]pyrrole-1-carboxylate.

14. A compound of claim 3, wherein $R_2$ is ethyl, namely 5-(4-ethylbenzoyl)-6-methylthio-1,2-dihydro-3H-pyrrolo[1,2-a]pyrrole-1-carboxylic acid and the pharmaceutically acceptable, non-toxic esters and salts thereof.

15. The methyl ester of the compound of claim 14, namely methyl 5-(4-ethylbenzoyl)-6-methylthio-1,2-dihydro-3H-pyrrolo[1,2-a]pyrrole-1-carboxylate.

16. A compound of claim 3, wherein $R_2$ is ethoxy, namely 5-(4-ethoxybenzoyl)-6-methylthio-1,2-dihydro-3H-pyrrolo[1,2-a]pyrrole-1-carboxylic acid and the pharmaceutically acceptable, non-toxic esters and salts thereof.

17. The methyl ester of the compound of claim 16, namely methyl 5-(4-ethoxybenzoyl)-6-methylthio-1,2-dihydro-3H-pyrrolo[1,2-a]pyrrole-1-carboxylate.

18. A compound of claim 3, wherein $R_2$ is i-propoxy, namely 5-(4-i-propoxybenzoyl)-6-methylthio-1,2-dihydro-3H-pyrrolo[1,2-a]pyrrole-1-carboxylic acid and the pharmaceutically acceptable, non-toxic esters and salts thereof.

19. The methyl ester of the compound of claim 18, namely methyl 5-(4-i-propoxybenzoyl)-6-methylthio-1,2-dihydro-3H-pyrrolo[1,2-a]pyrrole-1-carboxylate.

20. A compound of claim 3, wherein $R_2$ is methylthio, namely 5-(4-methylthiobenzoyl)-6-methylthio-1,2-dihydro-3H-pyrrolo[1,2-a]pyrrole-1-carboxylic acid and the pharmaceutically acceptable, non-toxic esters and salts thereof.

21. The methyl ester of the compound of claim 20, namely methyl 5-(4-methylthiobenzoyl)-6-methylthio-1,2-dihydro-3H-pyrrolo[1,2-a]pyrrole-1-carboxylate.

22. A compound of claim 3, wherein $R_2$ is trifluoromethyl, namely 5-(4-trifluoromethylbenzoyl)-6-methylthio-1,2-dihydro-3H-pyrrolo[1,2-a]pyrrole-1-carboxylic acid and the pharmaceutically acceptable, non-toxic esters and salts thereof.

23. The methyl ester of the compound of claim 22, namely methyl 5-(4-trifluoromethylbenzoyl)-6-methylthio-1,2-dihydro-3H-pyrrolo[1,2-a]pyrrole-1-carboxylate.

24. A compound of claim 3, wherein $R_2$ is cyclohexyl, namely 5-(4-cyclohexylbenzoyl)-6-methylthio-1,2-dihydro-3H-pyrrolo[1,2-a]pyrrole-1-carboxylic acid and the pharmaceutically acceptable, non-toxic esters and salts thereof.

25. The methyl ester of the compound of claim 24, namely methyl 5-(4-cyclohexybenzoyl)-6-methylthio-1,2-dihydro-3H-pyrrolo[1,2-a]pyrrole-1-carboxylate.

26. A compound of claim 3, wherein $R_2$ is n-propyl, namely 5-(4-n-propylbenzoyl)-6-methylthio-1,2-dihydro-3H-pyrrolo[1,2-a]pyrrole-1-carboxylic acid and the pharmaceutically acceptable, non-toxic esters and salts thereof.

27. The methyl ester of the compound of claim 26, namely methyl 5-(4-n-propylbenzoyl)-6-methylthio-1,2-dihydro-3H-pyrrolo[1,2-a]pyrrole-1-carboxylate.

28. A compound of claim 3, wherein $R_2$ is cyclopropyl, namely 5-(4-cyclopropylbenzoyl)-6-methylthio-1,2-dihydro-3H-pyrrolo[1,2-a]pyrrole-1-carboxylic acid and the pharmaceutically acceptable, non-toxic esters and salts thereof.

29. The methyl ester of the compound of claim 28, namely methyl 5-(4-cyclopropylbenzoyl)-6-methylthio-1,2-dihydro-3H-pyrrolo[1,2-a]pyrrole-1-carboxylate.

30. A compound of claim 2, wherein $R_1$ is methylsulfinyl.

31. A compound of claim 30, wherein $R_2$ is bromo, namely 5-(4-bromobenzoyl)-6-methylsulfinyl-1,2-dihydro-3H-pyrrolo[1,2-a]pyrrole-1-carboxylic acid and the pharmaceutically acceptable, non-toxic esters and salts thereof.

32. The methyl ester of the compound of claim 31, namely methyl 5-(4-bromobenzoyl)-6-methylsulfinyl-1,2-dihydro-3H-pyrrolo[1,2-a]pyrrole-1-carboxylate.

33. A compound of claim 2, wherein $R_1$ is methylsulfonyl.

34. A compound of claim 33, wherein $R_2$ is bromo, namely 5-(4-bromobenzoyl)-6-methylsulfonyl-1,2-dihydro-3H-pyrrolo[1,2-a]pyrrole-1-carboxylic acid and the pharmaceutically acceptable, non-toxic esters and salts thereof.

35. The methyl ester of the compound of claim 34, namely methyl 5-(4-bromobenzoyl)-6-methylsulfonyl-1,2-dihydro-3H-pyrrolo[1,2-a]pyrrole-1-carboxylate.

36. A compound of claim 1, selected from the group of compounds represented by formula (2).

37. A compound of claim 36 wherein X is oxygen.

38. A compound of claim 36 wherein X is sulfur.

39. A compound of claim 36 wherein X is NH.

40. A compound of claim 36 wherein X is $NR_3$.

41. An anti-inflammatory or analgesic composition for treating inflammation or pain in mammals which comprises a pharmaceutically acceptable non-toxic excipient and a therapeutically effective amount of a compound of claim 1.

42. A method for treating inflammation or pain in mammals which method comprises administering to a mammal in need thereof a therapeutically effective amount of compound of claim 1.

* * * * *